United States Patent [19]

Katoh et al.

[11] Patent Number: 5,342,610

[45] Date of Patent: Aug. 30, 1994

[54] BENZOPHENONE DERIVATIVE, ULTRAVIOLET ABSORBENT AND EXTERNAL PREPARATION FOR SKIN

[75] Inventors: Mikiko Katoh; Keiichi Uehara; Sadaki Takata, all of Yokohama, Japan

[73] Assignee: Shiseido Co., Ltd., Tokyo, Japan

[21] Appl. No.: 963,901

[22] Filed: Oct. 20, 1992

[30] Foreign Application Priority Data

Oct. 21, 1991 [JP] Japan ................................ 3-301076
Sep. 4, 1992 [JP] Japan ................................ 4-262962

[51] Int. Cl.$^5$ ..................... F61K 7/42; C07H 15/24
[52] U.S. Cl. ............................... 424/59; 424/78.03; 536/18.1
[58] Field of Search ............... 536/18.1; 424/59, 78.03

[56] References Cited

U.S. PATENT DOCUMENTS 3,415,875 12/1968 Luethi et al. .

FOREIGN PATENT DOCUMENTS 1481633 3/1966 France .
2307820 3/1976 France .
58-110535 7/1983 Japan .
1186818 11/1968 United Kingdom .

OTHER PUBLICATIONS

Biochim Biophys Acta 946 (1988) 75-84 Holman et al.

*Primary Examiner*—Herbert J. Lilling
*Attorney, Agent, or Firm*—Townsend & Banta

[57] ABSTRACT

Benzophenone derivatives expressed by the following general expression (1):

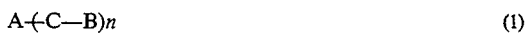

wherein $\underline{A}$ in the above general expression (1) is a residual group obtained by removing one hydroxyl group from sugar or sugar alcohol, and $\underline{B}$ is a benzophenone group shown by the following general expression (2)

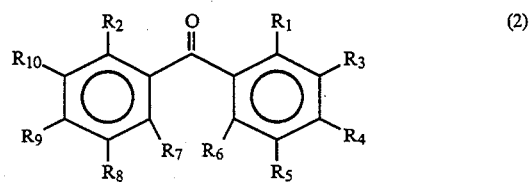

wherein $R_1$ through $R_{10}$ each is expressed by hydrogen, hydroxyl group, an alkoxy group, or the aforesaid binder $\underline{C}$, and at least one of them is the binder $\underline{C}$. In the case of an alkoxy group, preferably the number of carbon atoms is 1 to 4.

$\underline{C}$ is equivalent to —O—R— ($\underline{O}$ is oxygen, $\underline{R}$ is a fatty chain, and the number of carbon atoms therein is preferably 1 to 4), or 1 mole of glycerin with one hydroxyl group therein bound to $\underline{A}$ and another hydroxyl group to $\underline{B}$. The benzophenone derivatives according to the present invention have excellent capability to absorb ultraviolet rays as well as high compatibility with polar solvent. Also the external preparation for skin in which the benzophenone derivatives are mixed can be mixed in a polar base with wide availability for industrial purpose.

9 Claims, 20 Drawing Sheets

BENZOPHENONE DERIVATIVE, ULTRAVIOLET ABSORBENT AND EXTERNAL PREPARATION FOR SKIN

FIELD OF THE INVENTION

This invention relates to a benzophenone derivative, an ultraviolet absorbent and an external preparation for skin or more particularly, a benzophenone derivative having a high solubility in water, and an ultraviolet absorbent and an external preparation for skin using the benzophenone derivative.

BACKGROUND OF THE INVENTION

Most of ultraviolet ray normally received by a human body comes from sunlight. The ultraviolet ray included in sunlight is divided to a long wavelength ultraviolet ray having a wavelength from 400 nm to 320 nm (UV-A), a medium wavelength ultraviolet ray having a wavelength from 320 nm to 290 nm (UV-B), and a short wavelength ultraviolet ray having a wavelength of not more than 290 nm in a field of skin science. Of these, the ultraviolet rays having a wavelength of not more than 290 nm are absorbed by the ozonosphere and does not reach the surface of the earth.

The ultraviolet rays reaching the surface of the earth give various influences to human skin. Of the ultraviolet rays reaching the surface of the earth, the UV-A makes color of human skin brown, reduces the elasticity of skin, and promote generation of wrinkles, thus causing rapid aging of human skin. Also the ultraviolet rays promote start of the erythema reaction, or further stimulates this reaction in certain types of patients, and furthermore sometimes may cause photo-toxicity or photo allergy reactions. On the other hand, also UV-B forms erythema or blister on human skin, and causes aggravation of melanin formation or other changes such as deposition of pigments.

For the reasons as described above, in order to prevent aging of human skin and generation or increase of wrinkles and flecks thereon, it is very important to protect human skin from the ultraviolet rays, and various types of ultraviolet absorbent have been developed for that purpose.

The existing ultraviolet absorbents used for practical application include a PABA derivative, a cinnamic acid derivative, a salicylic acid derivative, a benzophenone derivative, a urocanine derivative, a campher derivative, and heterocyclic derivatives.

These types of ultraviolet absorbent are generally mixed in external preparations for skin such as cosmetics, or quasidrugs, and a low molecular weight dimethyl-siloxane base has been widely used as a base for the external preparation for skin.

Namely, as anti-suntan agent are most frequently used during summer, oily bases have been used because of their anti-sweat property as well as their high water resisting property, and as a result, most of materials which have been used for ultraviolet absorbents are oil soluble.

Recently, however, social attention has been focused on effects of ultraviolet rays on human skin in our daily life, so that anti-suntan materials are desired for ordinary skin care. For that purpose, development of materials which are water soluble and at the same time absorb ultraviolet rays has been strongly demanded, because such materials can mixed in aqueous external preparation such as skin lotion in a large volume, and also because a large volume of ultraviolet absorbent is required to be mixed in the entire system to realize a external preparations having the high capability to absorb ultraviolet rays, which makes it necessary to mix a ultraviolet absorbent not only in oil phase but also in aqueous phase.

The prior types of ultraviolet absorbent, however, are oil soluble in most cases, and their solubility in water is very low, and their applications have been limited to a relatively narrow area. As a water soluble ultraviolet absorbent, only 2-hydroxy-4-methoxy-5-sulfoxonium benzophenone sodium salt has been known, and as this is a salt, it effects pH of the formula system.

DISCLOSURE OF THE INVENTION

This invention was made to solve the problem in the prior art as described above, and the object is to provide a water soluble material having a high ultraviolet absorptivity and an external preparation for skin in which the material is mixed.

The invention made strenuous efforts to achieve the object as described above, and found that a certain benzophenone derivative had an ultraviolet absorptivity as well as a compatibility with polar solvent, thus completing the present invention.

The benzophenone derivative described in the claim 1 in the present application is expressed by the following general expression (1), $$A\text{-}(C\text{--}B)_n \qquad (1)$$

In the general expression (1) above, $\underline{A}$ is a residual group obtained by removing a hydroxyl group from sugar or sugar alcohol, while $\underline{B}$ is a benzophenone group which is expressed by the following general expression (2).

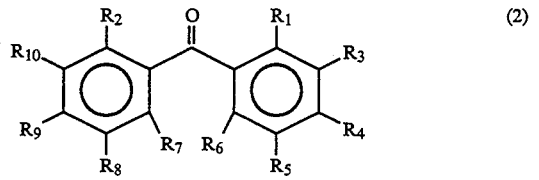

wherein each of $R_1$ to $R_{10}$ are expressed by hydrogen, a hydroxyl group, alkoxy group, or the aforesaid binder $\underline{C}$, and at least one of them is a binder $\underline{C}$. In case of an alkoxy group, the number of carbon atoms is preferably in a range from 1 to 4.

$\underline{C}$ is —O—R— (O is oxygen, while R is a fatty chain preferably having 1 to 4 carbon atoms), or 1 mole of glycerin. In case of glycerin, one of the hydroxyl groups is bound to $\underline{A}$ and another hydroxyl group is bound to $\underline{B}$.

n is 1 or other integer.

The ultraviolet absorbent described in the claim 2 is characterized in that at least one type of benzophenone derivatives expressed by the general expression (1) above are included therein.

The external preparation for skin described in the claim 3 is characterized in that at least one of the benzophenone derivative expressed by the general expression (1) above are included therein.

Also, the benzophenone derivative described in the Claim 4 in the present application is expressed by the following general expression (3).

$$A(C\text{--}B)_n \qquad (3)$$
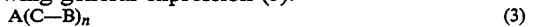

Herein, A is sugar or sugar alcohol, C is 1 mole of glycerin wherein one of the hydroxyl groups is bound to A and another hydroxyl group is bound to B.

B is a benzophenone group expressed by the following general expression (4).

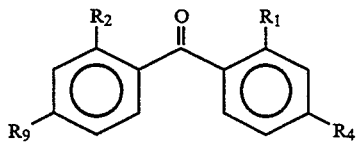  (4)

(In the general expression (4), at least one of $R_1$ through $R_9$ is a group bound to C, and others are hydrogen or a hydroxyl group, an alkyl group, or an alkoxyl group.

n or other integer.

The ultraviolet absorbent described in the Claim 5 is characterized in that at least one type of the benzophenone derivatives expressed by the general expression (3) above is included therein.

The external preparation for skin described in Claim 6 is characterized in that at least one of the benzophenone derivatives expressed by the general expression (3) above is included.

In the general expression (3) above, A is a residual group of sugar or sugar alcohol, and examples of the sugar include mono saccharides such as glucose, galactose, xylose, fructose, altose, talose, mannose, arabinose, idose, lyxose, ribose, allose, gulose, erythrose, threose, tagatose, sorbose, psicose, xylulose, ribulose, erythrulose, fucose, rhamnose and a mixture thereof; disaccharide such as maltose, isomaltose, lactose, xylobiose, gentiobiose, kojiobiose, cellobiose, sohorose, nigerose, sucrose, melibiose, laminaribiose, rutinose, lactulose, palatinose, turanose, trehalose and a mixture thereof; or trisaccharides such as maltotriose, meleziose, raffinose and a mixture thereof; furthermore higher polysaccharide and a mixture thereof; and also a mixture of the monosacchride, disaccharide, and higher polysaccharide can be used for this purpose. On the other hand, examples of sugar alcohol include sugar alcohol such as maltitol, sorbitol, mannitol, galactitol, glucitol, inositol, maltitriol, threitol, arabinitol, alcritol and a mixture thereof, or higher polysaccharide and a mixture thereof, and also a mixture of these sugar alcohol can be used for this purpose. Furthermore, the same effect can be achieved by using a mixture of the monosaccharide, disaccharide, higher polysaccharide, and sugar alcohol.

In the general expression (4) which expresses a benzophenone group B, each of $R_1$ to $R_9$ expresses a bond group to hydrogen or hydroxyl group, an alkyl group or an alkoxyl group, or a bond group to C. In case of an alkyl group or an alkoxyl group, the fatty chain may be any of a straight chain alkyl group, a branch chain alkyl group, an unsaturated alkyl group and a cycloalkyl group, and example of the fatty chain include a methyl group, an ethyl group, an acetynyl group, a propyl group, an isopropyl group, a propenyl group, a butyl group, an isobutyl group, a t-butyl group, and a butenyl group. Wavelength of absorbed ultraviolet rays does not differ remarkably in any case, but a methyl group and a ethyl group are especially preferable because of their industrial applicability.

C is a glyceril group which is equivalent to 1 mole of glycerin, and any form of bond may be added.

n indicates an integer, and preferably indicates any of 1 to 3 because of the water solubility.

As the benzophenone derivatives described above are in solid or syrupy state and are extremely excellent in their safety and stability, the materials can be mixed in chemical products such as dye or ink, plastics, coating agent, and chemical textile, and in addition they can be mixed in pharmaceutical products, quasidrug products, cosmetics and cleaning agents as a component. Furthermore, the materials feature the excellent capability to preserve humidity.

The benzophenone derivative expressed by the general expression (3) can be produced by, for instance, glycydilating hydroxy benzophenone expressed by the general expression (5) and reacting the resultant glycidyloxy benzophenone expressed by the general expression (6) with sugar or sugar alcohol according to the method described in the Japanese Patent Application No. 180989/1986.

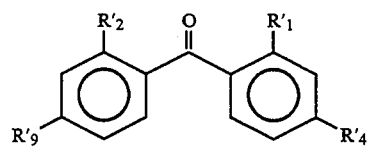  (5)

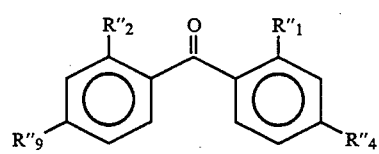  (6)

For instance, the derivative can be synthesized as follows.

The compound expressed by the general expression (6) can be synthesized by reacting the compound expressed by the general expression (5) according to the method developed by Sandlere et. al., (S. R. Sandler, F. R. Berg, J. Appl. Polymer. Soc. 9,3707(1965)), or according to the method developed by Robert et. al., (Tetrhedorn, 35, 2169-2172 (1979)). Namely, the compound expressed by the general expression (6) can be synthesized by dissolving or suspending the compound expressed by the general expression (5) in a non-aqueous solvent such as dimethylsulfoxide, dimethylformamide, dioxan, dimethylacetamide, N-methylpyrrolidone, N-acctylmorpholine, N-methyl succinic acid imid, or by dissolving or suspending the compound expressed by the general expression (5) in acetone aqueous solvent, or by mixing the compound expressed by the general expression (5) with epichlorohydrin under the temperature from 90° to 130° C. in the presence of a catalyst without using any solvent. This reaction may be carried out under flow of such a gas as argon, and one or more compounds expressed by the general expression (5) may be used in this reaction.

The catalysts available in this reaction include a Lewis Acidic Catalyst such as $BF_3 \cdot Et_2O$ or aluminum trichloride; acidic catalyst such as p-toluene sulfonic acid, heteropoly phosphoric acid, chloric acid, sulfuric acid; alkali such as sodium hydroxide, potassium hydroxide, potassium carbonate, sodium carbonate, sodium hydride, sodium alcoholate; and amine such as N-methylbenzyl amine.

The compound expressed by the general expression (3) can be manufactured by reacting the compound expressed by the general expression (4) to sugar or sugar alcohol according to, for instance, the method described in Japanese Patent Application No. 180989/1986.

For instance, the following method is applicable. Sugar or sugar alcohol may be dissolved or suspended in a non-aqueous solvent such as dimethylsulfoxide, dimethylformamide, dioxan, dimethylacetamide, N-Methylpyrrolidone, N-acetylmorpholine, or N-methylsuccinimid, and mixed and stirred with the compound expressed by the general expression (6) under the temperature from 90° to 130° C. in the presence of a catalyst. This reaction may be carried out under a flow of gas such as $N_2$ or argon, and also one or more compounds expressed by the general expression (6) may be used in this reaction.

The catalysts available in this reaction include a acidic catalyst such as p-toluene sulfonic acid, heteropoly phosphoric acid, chrolic acid, or sulfonic acid; alkali catalyst such as sodium hydrate, potassium hydrate, potassium carbonate, sodium carbonate, sodium alcoholate; salt such as ammonium chloride, or sodium chloride; and amine such as N-methylbenzylamine.

The mole ratio of sugar or sugar alcohol vs. the compound expressed by the general expression (6) to be used in this reaction should preferably be 1:1 to 3:1 when it is necessary to obtain monoether as a main product, and more preferably be in a range from 2:1 to 3:1. If the mole ratio of sugar or sugar alcohol and the compound expressed by the general expression (6) is out of the ranges described above; namely if sugar or sugar alcohol is too little, impurities such as tetraether would be easily generated, and if sugar or sugar alcohol is too much, a large volume of the material would remain after the reaction, which affects purification of the product, and it is not preferable.

When acid or alkali is used as a catalyst, acid such as acetic acid, chloric acid, sulfuric acid, or phosphoric acid, or alkali such as sodium hydrate or potassium hydrate should be added to neutralize the catalyst in the reaction system after all of the compound expressed by the general expression (6) is consumed.

After the reaction as described above, the reactant solvent may be depressurized and removed, the product may be used as it is or may be diffused in a solvent for use, or may be purified according to the column chromatography or the recrystalizing method.

In the resultant product obtained as described above, in addition to the benzophenone expressed by the general expression (3), compounds wherein n in the general expression (3) is 4 or more, salt, sugar or sugar alcohol not reacted yet may coexist. For this reason, in order to remove the sugar or sugar alcohol or salt therefrom, the product may be purified by extracting with a solvent such as methyl alcohol, ethyl alcohol, butyl alcohol, isopropyl alcohol, or by diffusing it in a mixture of water and methylethyl ketone having a large volume of salt therein and fractionating the organic solvent layer. Also in order to remove sugar or sugar alcohol and salt for separating the compound, the resultant product may be purified by dissolving or suspending the resultant product in water or a mixture of water and alcohol, passing it at first through water in a opposite phase partition column such as hyper porous polymer (such as Hi-porous resin supplied from Mitsubishi Kasei Kogyo Kabushiki Kaisha) or octadecyl silica, and then through a mixed solution of water with alcohol such as methanol or ethanol or a polar organic solvent such as acetonitrile, and fractionating and taking out this liquid. Also the resultant product can be purified in an ordinary phase system according to the silica gel chlomatograph or other appropriate method.

By the way, it is preferable to use a ultraviolet absorbent in the form of aqueous solution in which a non-ionic hydrophilic group has been introduced for the purpose to reduce its effect over pH of the entire reaction system. As a non-ionic hydrophilic group, mainly polyethylene oxide, polyglycerin, or sugar can be considered. Of these, polyethylene oxide is decomposed as time goes by and generates formalin, and dioxan is contained in it, so recently the material is regarded as not preferable for safety. From this point of view, polyglycerin or sugar is preferable because the safety is very high. On the other hand, it is desired that the base consists of a single components, but polyethylene oxide or polyglycerin is apt to form a mixture having inhomogenious distribution because of the characteristics in the systhesizing reaction for the materials, and also purification of the material is not so easy. In contrast to it, products of a hydrophilic group such as sugar are hard to form a mixture, and also the purification is easy, so that it is preferable.

However, in such processes as direct etherification or direct esterification of sugar, also a mixture having distributed mole numbers of added components is easily generated, which is troublesome.

So the inventors further developed the following benzophenone derivative to solve the problems as described above.

Namely, the benzophenone derivative described in the Claim 7 in this application is expressed by the following general expression (7),

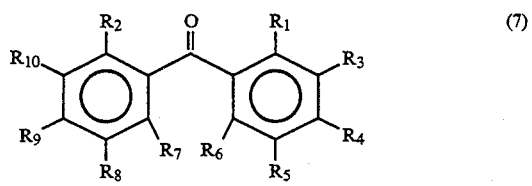

(7)

wherein $R_1$ and $R_2$ are hydrogen or hydroxyl group, and at least one of them is expressed by a hydroxyl group.

$R_3$ through $R_{10}$ are expressed by hydrogen, a hydroxyl group, an alkoxy group, or —O—R—A, and at least one of them is expressed by —O—R—A. In case of an alkoxy group, preferably the number of carbon atoms is in a range from 1 to 4. $\underline{A}$ is a residual group obtained by removing one hydroxyl group from sugar, $\underline{R}$ is a fatty chain, and preferably the total number of carbon atoms is in a range from 1 to 4.

The ultraviolet absorbent described in the Claim 8 is characterized in that said ultraviolet absorbent contains one or more types of benzophenone derivatives expressed by the aforesaid general expression (7).

The external preparation for skin described in the Claim 9 is characterized in that said external preparation contains one or more types of benzophenone derivatives expressed by the aforesaid general expression (7).

In the general expression (7) above, $\underline{A}$ is a residual group of sugar, and examples of the sugar include monosaccharide such as glucose, galactose, xylose, fructose, altrose, talose, mannose, arabinose, idose, lyxose, ribose, allose, gulose, erythrose, threose, tagatose, sorbose, psicose, xylulose, ribulose, erythrulose, fucose, rhamnose and a mixture thereof; disaccharide such as maltose, isomaltose, lactose, xylobiose, gentiobiose, kojiobiose, cellobiose, sohorose, nigerose, sucrose, melibiose, laminaribiose, rutinose, lactulose, palatinose, turanose, trehalose and a mixture thereof; or trisaccharides such as maltotriose, meleziose, raffinose and a mixture thereof; furthermore higher polysaccharide and a mixture thereof, disaccharide, and higher polysaccharide can be used for this purpose.

In $R_3$ through $R_{10}$, if O—R—A is used, the fatty chain as $\underline{R}$ may be any of a straight chain alkyl group, a branch chain alkyl group, an unsaturated alkyl group, and a cycloalkyl group, and example of the fatty chain include a methyl group, an ethyl group, an acetynyl group, a propyl group, an isopropyl group, a propenyl group, a butyl group, an isobutyl group, a t-butyl group, a butenyl group. Wavelength of absorbed ultraviolet rays does not differ remarkably in any case, but a methyl group and a ethyl group are especially preferable because of their industrial applicability. Also, in $R_3$ to $R_{10}$, if an alkoxy group is used, also a fatty chain in said alkoxy group may be any of a straight chain alkoxy group, a branch chain alkoxy group, an unsaturated alkoxy group, and a cycloalkoxy group, and examples include a methoxy group, an ethoxy group, a acetoxy group, a propyroxy group, an isopropyroxy group, a propenyloxy group, a butyloxy group, an isobutyloxy group, a t-butyroxy group, and a bytenyloxy group. Wavelength of absorbed ultraviolet rays in any of the compounds above does not differ remarkably, but especially the methoxy group and the ethoxy group are preferable because of their high solubility in water or excellent applicability for industrial purpose.

The benzophenone derivatives are in solid state and are extremely excellent in their safety and stability, so the materials can be mixed in chemical products such as dye or ink, plastics, coating agents, and chemical textiles, and in addition they can be mixed as components in pharmaceutical products, quasidrug products, cosmetics, and cleaning agents.

The benzophenone derivatives relating to the general expression (7) can be synthesized by using the acidic catalyst for denaturing sugar described in the Japanese Patent Laid Open Publication No. 84637/1988, or through a reaction generally used for glycosylation (such as Kenich-Knol reaction, Helferich method, or other ether exchanging method).

For instance, the benzophenone derivatives relating to the general expression (7) above can be synthesized as follows.

To obtain the above materials, acetylate of sugar is dissolved in a non-polarized solvent such as dibutyl cellosolve or toluene, or a compound expressed by the general expression (8)

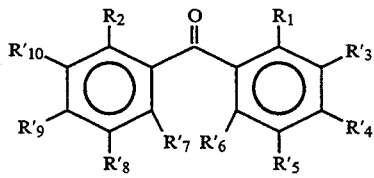

(8)

(wherein $R_1$ and $R_2$ are the same as the aforesaid compounds (2) above, $R'_3$ through $R'_{10}$ are expressed by hydrogen, hydroxyl group, an alkoxy group, or O—R—OH, and at least one of them is expressed by O—R—OH. The number of carbon atoms in the alkoxy group is preferably from 1 to 4, and R is a fatty chain having 1 to 4 carbon atoms) is added and stirred under the temperature from 90° to 130° C. in the presence of a acidic catalyst. The reaction is carried out in a depressurized state, and 2 or more compounds expressed by the general expression (8) may be used in this reaction.

The catalysts available in this reaction include p-toluene sulfonic acid, heteropoly phosphoric acid, zinc acetate, zinc chloride, or ion-exchange resin.

After the reaction, the reactant solvent is distillated under reduced pressure condition for removal and the product is extracted with toluene, and then washed with water. The resultant extracted liquid may be condensed under reduced pressure condition and then deacetylated as it is or may be purified according to the silica gel column chromatography and then deacetylated.

In the resultant product thus obtained, in addition to the benzophenone derivatives expressed by the general expression (7), salt generated when neutralized, sugar and other materials coexist. For this reason, in order to remove, for instance, sugar and salt, the product can be purified by extracting it with a solvent which does not dissolve sugar such as methyl alcohol, ethyl alcohol, butyl alcohol, or isopropyl alcohol, or by diffusing it in a mixture of water containing a large volume of sugar, methylethyl ketone, and n-bythanol and fractionating the organic solvent layer. Also in order to remove sugar or sugar alcohol and salt for separating the compound, the resultant product may be purified by dissolving or suspending the resultant product in water or a mixture of water and alcohol, passing it at first through water in a opposite phase partition column such as hyper porous polymer (such as Hi-porous resin supplied from Mitsubishi Kasei Kogyo Kabushiki Kaisha) or octadecyl silica, and then through a mixed solution of water with alcohol such as methanol or ethanol, or polar organic solvent such as acetonitrile, and fractionating and taking out this liquid.

The benzophenone derivatives as described above may be used after the solvent for extraction is removed by means of distillation under reduced pressure condition or purified using a column, or may be used as it is.

The benzophenone derivatives thus obtained are excellent in their chemical stability and resistance against oxidation, and are also water soluble and can absorb ultraviolet rays in a wide range, and furthermore they are excellent in their capability to preserve humidity. As the benzophenone according to the present invention are excellent in their stability, the materials can be mixed in cosmetics or pharmaceutical drugs. In addition to the embodiments of the present invention, the materials can appropriately be mixed with other ordinary cosmetics and other components for pharmaceutical drugs. For instance, various types of hydro carbon such as fluidized paraffin, squalane, vaseline, cetyl alcohol, isostearyl alcohol, 2-ethyl hexanoic acid cetyl, 2-octyldodecyl alcohol, triisostearic acid glycerin, Macademian nuts oil, and lanolin; fats and oils, oily components such as wax, silicone, surface active agents, thickeners, neutralizers, antiseptics, germicides, antioxidants, powder components, perfumes, other ultraviolet absorbents, drugs, metallic sealant, and pH modifiers can be listed as such materials.

DESCRIPTION OF THE PREFERRED EMBODIMENTS

Figure 1:
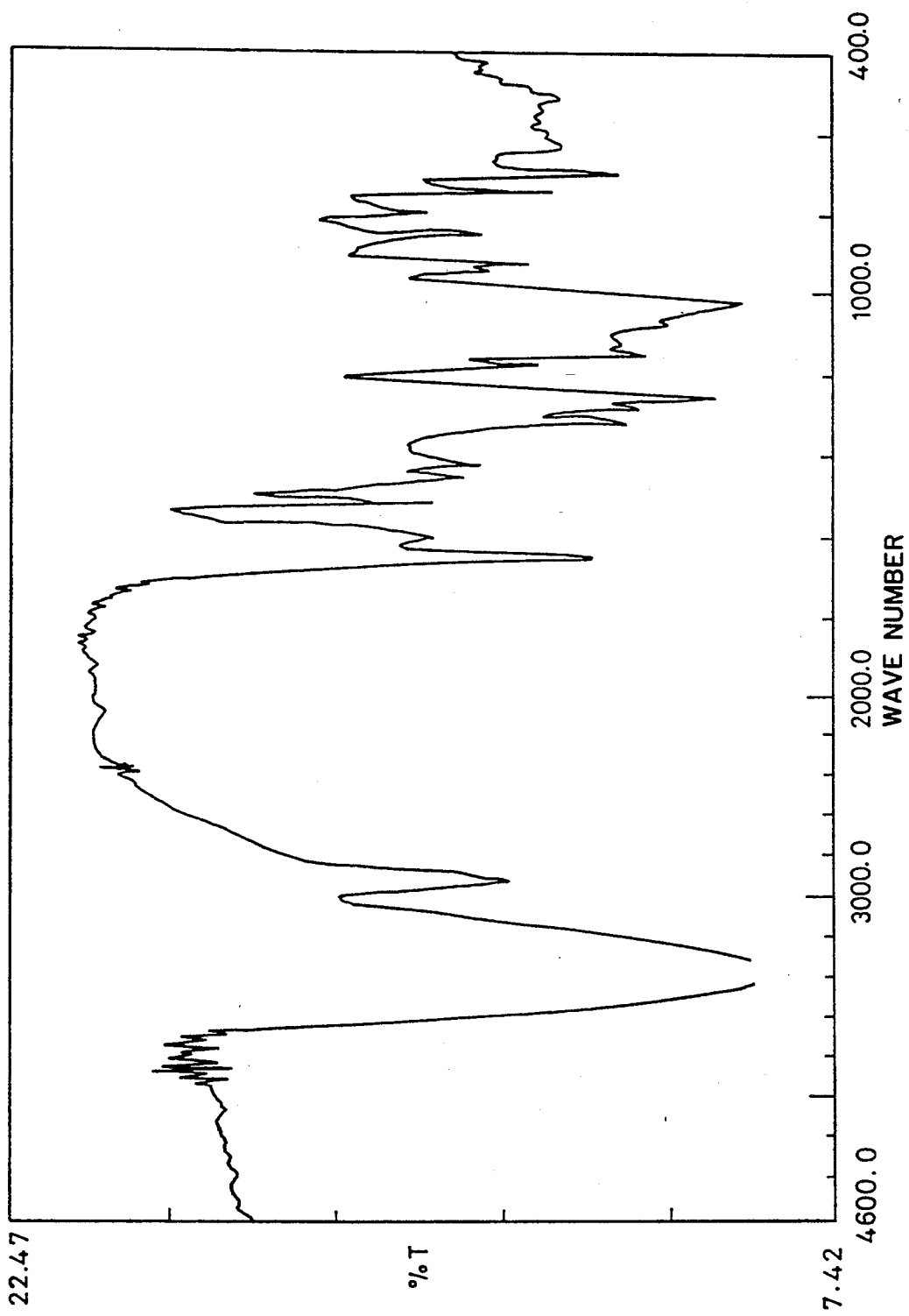
FIG. 1 is a chart of an infrared absorption spectrum of 1-(4-benzoylphenyl) glycerol maltitolether according to an embodiment of the present invention.

Description is made hereinafter for preferred embodiments of the present invention. It should be noted that the embodiment are not intended to limit the scope of the present invention. A unit for mixing rate is weight %.

Embodiment 1 1-(4-benzoylphenyl) glycerol maltitolether 1 g of 4-hydroxy benzophenone and 4.668 g of epichlorohydrin (0.025 mol) were dissolved, 20.5 mg of sodium hydroxide was added, and the reaction system was heated to 100° C. and then cooled to 95° C. Furthermore 201.4 mg of sodium hydroxide was added, and additional heating and agitation was carried out for 3 hours. The system was cooled to the room temperature, and salt was removed by filtering. The obtained filtrate was condensed under reduced pressure condition, and purified according to the silica gel chromatography to obtain 1.0 g of solid state 4-glycidyloxy benzophenone (Yield: 83%).

Then, 2.921 g of maltitol and 476.0 mg of potassium hydroxide were dissolved in 20 ml of dimethylsulfoxide, and the mixture was stirred under flow of nitrogen for 30 minutes. A solution obtained by dissolving 719 mg of the resultant 4-glycidyloxy benzophenone dissolved in 1 ml of dimethylsulfoxide was dripped to it. Furthermore, heating and agitation was continued for 1 hour under flow of nitrogen, and the reaction system was cooled to the room temperature and neutralize with chloric acid. The reaction system was fractionated according to the column chromatography using the hyperporous polymer (Hiporous resin supplied from Mitsubishi Kasei Kogyo Kabushiki Kaisha) at first as a developing solvent with purified water, and then a mixture of ethyl alcohol and purified water with the mixing ratio of 1:1, and effluent fraction in which the mixing ratio of ethyl alcohol and purified water was 1:1 was condensed to obtained 500 mg of 1-(4-benzoylphenyl) glycerol maltitolether (Yield: 30%).

(1) Infrared absorption spectroscopy

Measurement was made by using the IRA-1 infrared absorption spectrometer supplied from Nihon Bunko Kabushiki Kaisha with the KBr disk method, and absorption due to stretching vibration of the hydroxyl group at 3387 cm$^{-1}$, stretching vibration of the glyceroil group at 2928 cm$^{-1}$ and stretching vibration of the carbonyl group at 1649 cm$^{-1}$ were observed.

The results are shown in FIG. 1.

(2) $^{13}$C-NMR spectroscopy

Measurement was made by using CD$_3$OD as a solvent with JOEL GX-400 supplied from Nippon Denshi Kabushiki Kaisha at 35° C., and signal from carbon atoms in the benzophenone part was observed at δ197 ppm, 164 ppm, 139 ppm, 134 ppm, 133 ppm, 131 ppm, 129 ppm, and 115 ppm, and signals from the maltitol group and the glyceril group was observed in a range from 103 ppm to 62 ppm.

Figure 2:
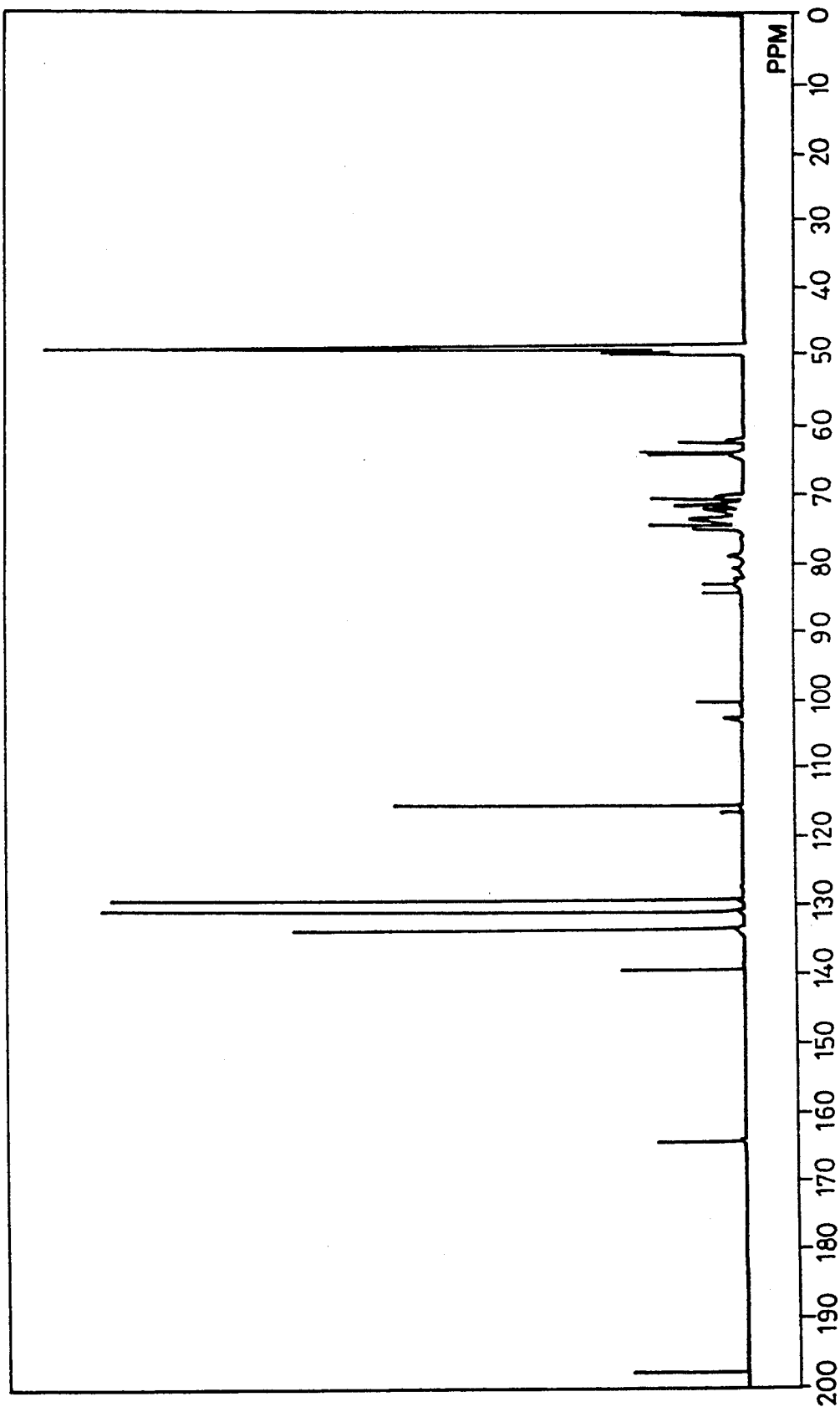
FIG. 2 is a chart of $^{13}$C-NMR spectrum of 1-(4-benzoylphenyl) glycerol maltitolether according to an embodiment of the present invention.

The results are shown in FIG. 2.

(3) $^{1}$H-NMR spectroscopy

Measurement was made by using CD$_3$OD as a solvent with JOEL GX-400 supplied from Nippon Denshi Kabushiki Kaisha under room temperature, and signals from hydrogen in the benzophenone section were observed in the range of δ7.8–7.1 ppm and signal from hydrogen in the maltitol group and glyceril group were observed in the range of δ5.2–3.3 ppm.

Figure 3:
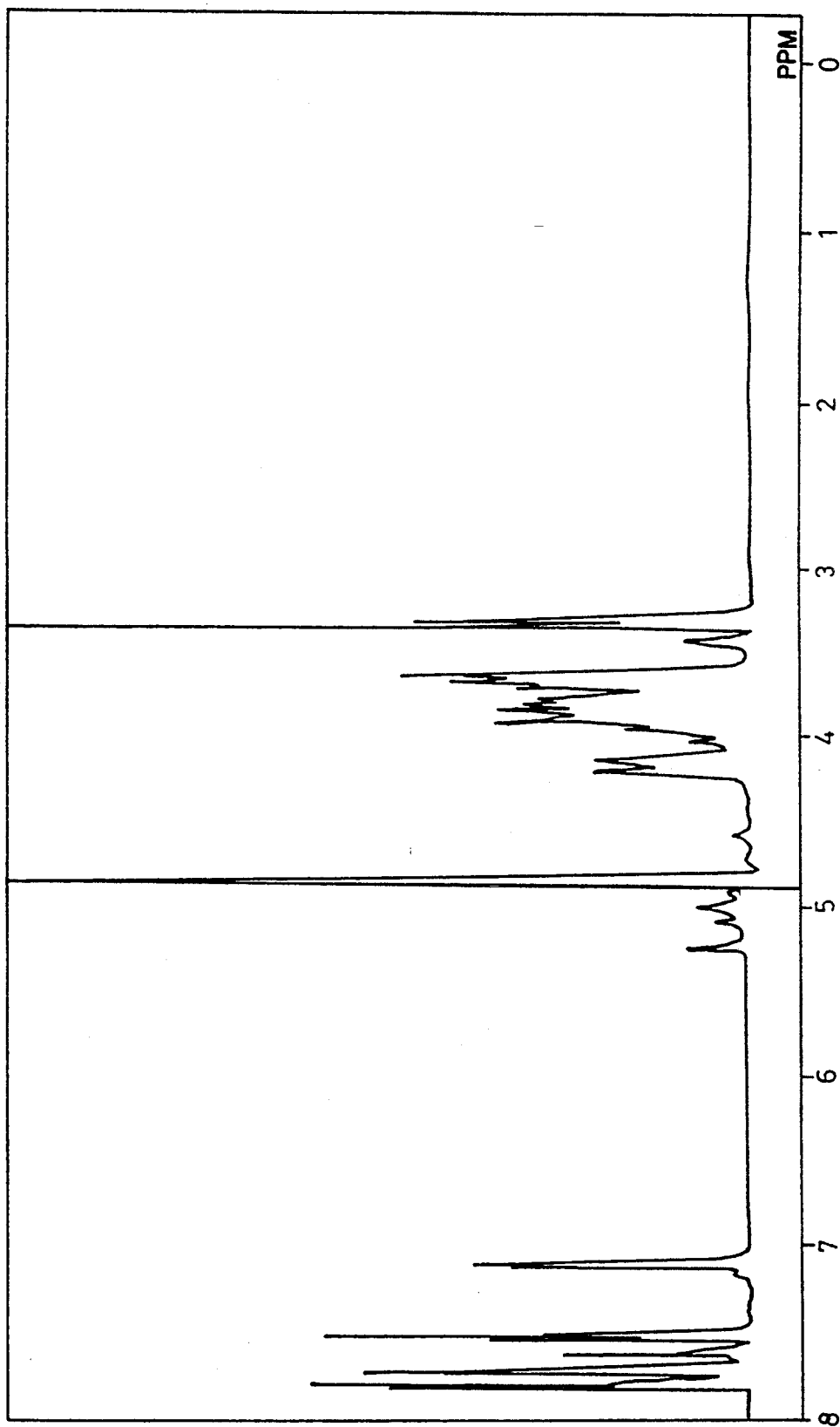
FIG. 3 is a chart of $^{1}$H-NMR spectrum of 1-(4-benzoylphenyl) glycerol maltitolether according to an embodiment of the present invention.

The results are shown in FIG. 3.

(4) Ultraviolet ray absorption spectroscopy

Measurement was made by using the UVIDEC 610 C ultraviolet ray absorption spectrometer from Nihon Bunko Kabushiki Kaisha with methanol as a solvent, and the peak absorption was observed at 282.7 nm.

Figure 4:
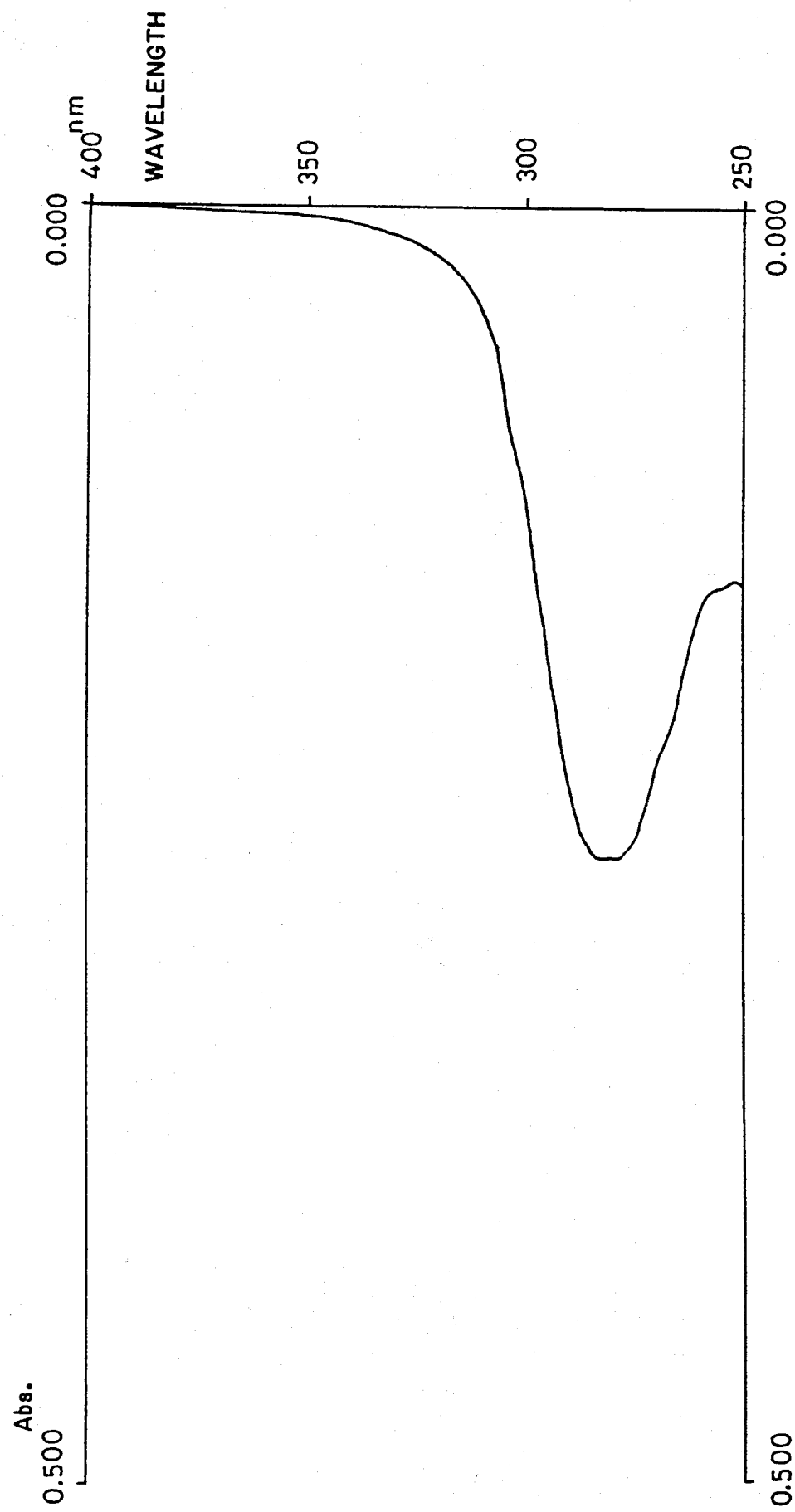
FIG. 4 is a chart of ultraviolet absorption spectrum of 1-(4-benzoylphenyl) glycerol maltitolether according to an embodiment of the present invention.

The results was shown in FIG. 4.

(5) Phenol indication

The product was spotted on TCL, phenol indicator was sprayed with a sprayer on it. 10% sodium carbonate solution was sprayed over it, but a color indicating presence of phenol was not observed.

Embodiment 2 1-(4-benzoyl-3-hydroxyphenyl) glycerolmaltitolether 3.0 g of 2,4-dihydroxy benzophenone and 15.5 g of epichlorohydrin (0.075 mol) were dissolved, and 112.0 mg of sodium hydroxide was added. The reaction system was heated to 100° C. and then cooled to 95° C., and 672.2 mg of sodium hydroxide was added. Additional heating and agitation was continued for 3 hours. Then, the reaction system was cooled to the room temperature, and salt was removed by filtering. The resultant filtrate was condensed under reduced pressure condition, and purified according to the silica gel column chromatography. 2.8216 g of solid state 4-glycidyloxy-2-hydroxy benzophenone was obtained (Yield: 75%).

Then, 1.550 g of maltitol and 84.2 mg of potassium hydroxide were dissolved in 10 ml of dimethylsulfoxide. The mixture was heated and stirred for 30 minutes under a flow of nitrogen, and a solution obtained by dissolving 406.0 mg of 4-glycidyloxy-2-hydroxy benzophenone in 6 ml of dimethylsulfoxide was dripped to it. Then, heating and agitation under flow of nitrogen was carried out for 1 hour, and then the reaction system was cooled to the room temperature and the mixture was neutralized by chloric acid. The reaction system was fractionated according to the column chromatography using the hyperporous polymer (Hiporous resin supplied from Mitsubishi Kasei Kogyo Kabushiki Kaisha) at the first time as a solvent with purified water, and then a mixture of ethyl alcohol and purified water with the mixing ratio of 1:1. Effluent fraction in which the mixing ratio of ethyl alcohol and purified water was 1:1 was condensed to obtain 478 mg of 1-(4-benzoyl-3-phenyl)glycerol maltitolether (Yield: 52%).

(1) Infrared absorption spectroscopy

Measurement was made by using the IRA-1 infrared absorption spectrometer supplied from Nihon Bunko Kabushiki Kaisha with the KBr disk method, and absorption due to stretching vibration of the hydroxyl group at 3380 cm$^{-1}$, stretching vibration of the hydrocarbon group at 2928 cm$^{-1}$ and stretching vibration of the carbonyl group at 1626 cm$^{-1}$ were observed.

Figure 5:
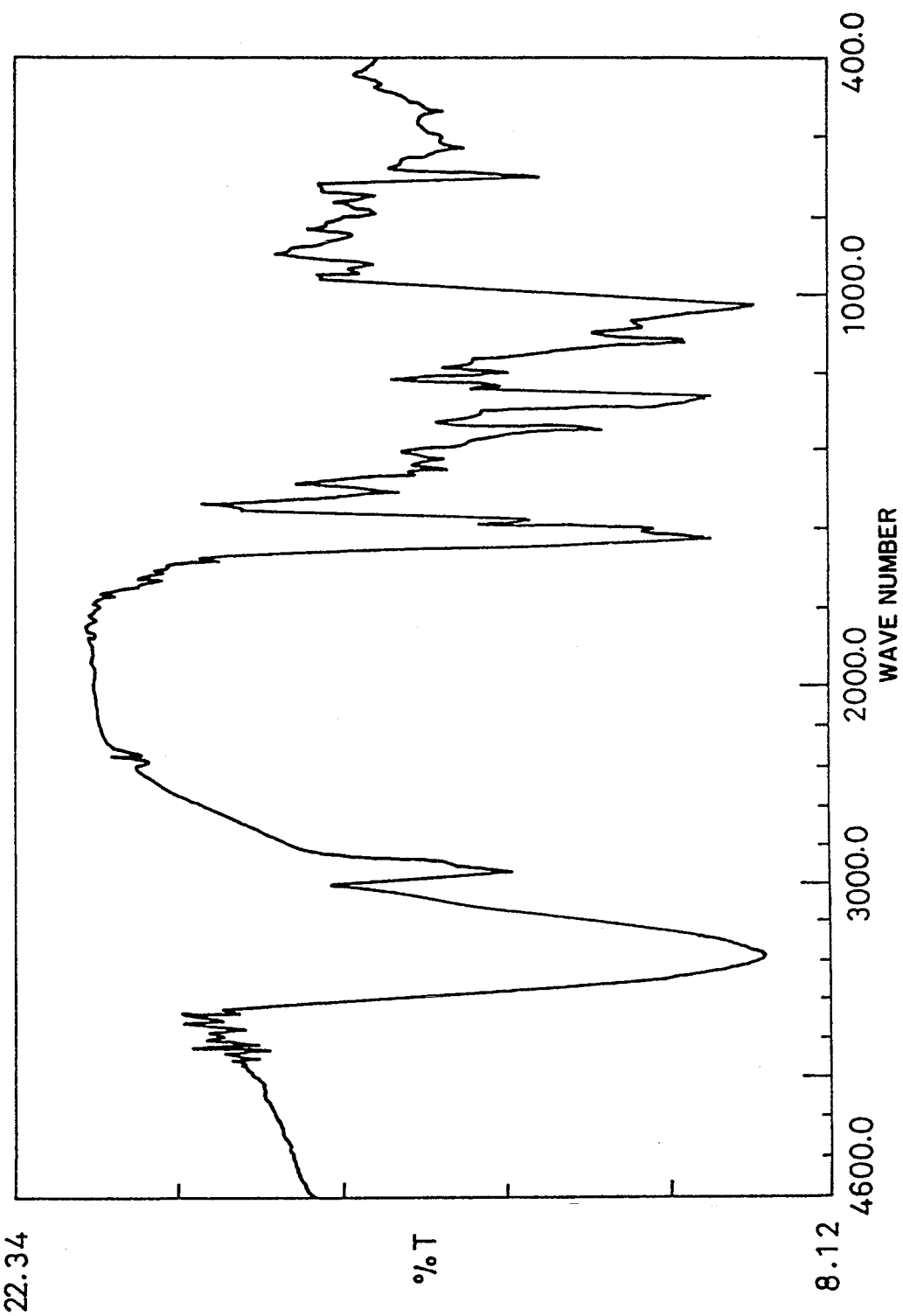
FIG. 5 is a chart of an infrared absorption spectrum of 1-(4-benzoyl-3-hydroxy-phenyl) glycerol maltitolether according to an embodiment of the present invention.

The results are shown in FIG. 5.

(2) $^{13}$C-NMR spectroscopy

Measurement was made by using CD$_3$OD as a solvent with JOEL GX-400 supplied from Nippon Denshi Kabushiki Kaisha at 35° C., and signal from carbon atoms in the benzophenone part was observed at δ201 ppm, 166 ppm, 139 ppm, 136 ppm, 133 ppm, 132 ppm, 130 ppm, 129 ppm and 114 ppm, and those from the carbons in the maltitol group and the glyceril group was observed in a range from 109 ppm to 62 ppm.

Figure 6:
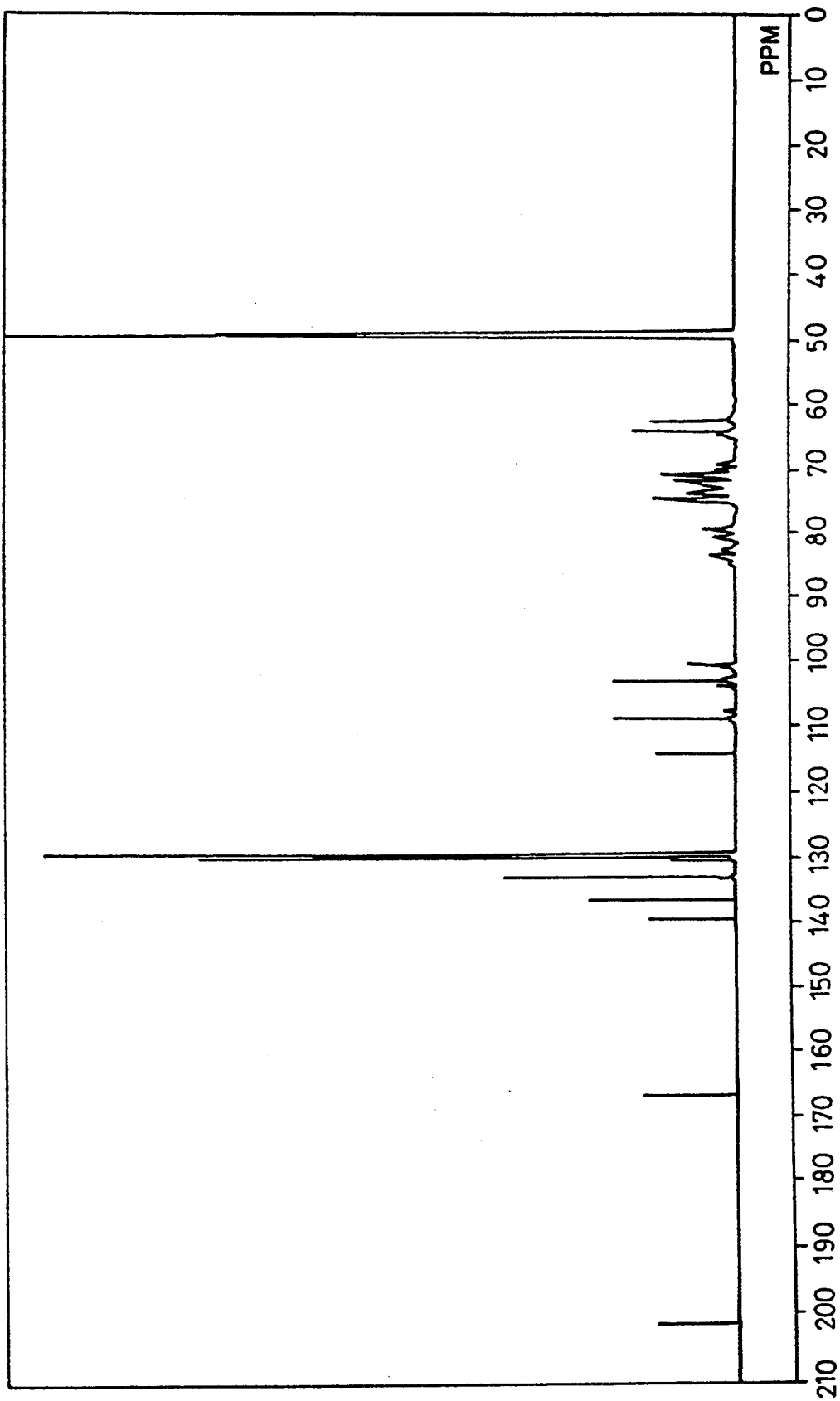
FIG. 6 is a chart of $^{13}$C-NMR spectrum of 1-(4-benzoyl-3-hydroxy-phenyl) glycerol maltitolether according to an embodiment of the present invention.

The results are shown in FIG. 6.

(3) $^1$H-NMR spectroscopy

Measurement was made by using CD$_3$OD as a solvent with JOEL GX-400 supplied from Nippon Denshi Kabushiki Kaisha, and signals from hydrogen in the benzophenone section were observed at δ12.5 ppm and in the range of δ7.8–7.1 ppm, and signal from hydrogen in the maltitol group and glyceril group were observed in the range of δ5.2–3.3 ppm.

Figure 7:
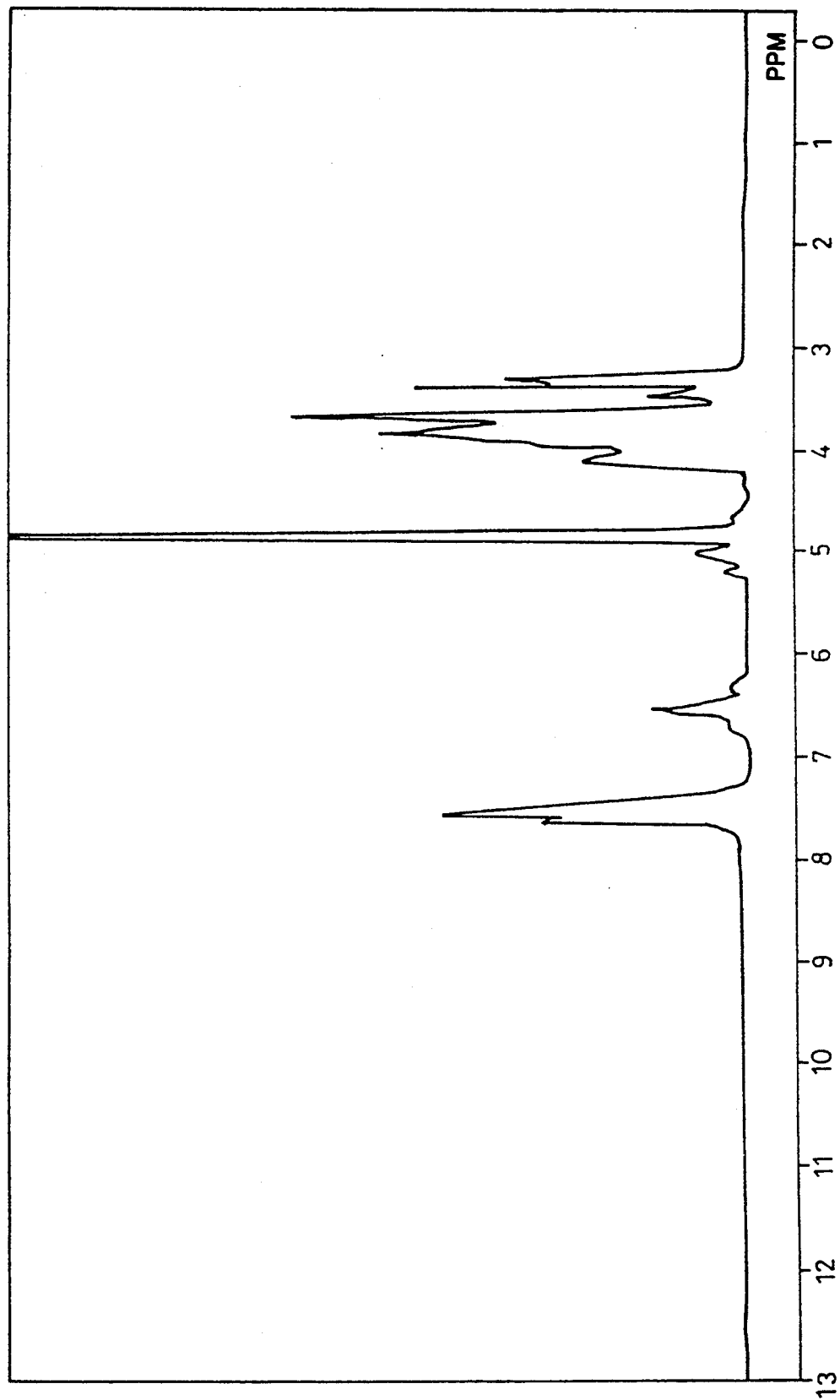
FIG. 7 is a chart of $^{1}$H-NMR spectrum of 1-(4-benzoyl-3-hydroxy-phenyl) glycerol maltitolether according to an embodiment of the present invention.

The resultant are shown in FIG. 7.

(4) Ultraviolet ray absorption spectroscopy

Measurement was made by using the UVIDEC 610 C ultraviolet ray absorption spectrometer from Nihon Bunko Kabushiki Kaisha with methanol as a solvent, and the peak absoption was observed at 279.8 nm.

Figure 8:
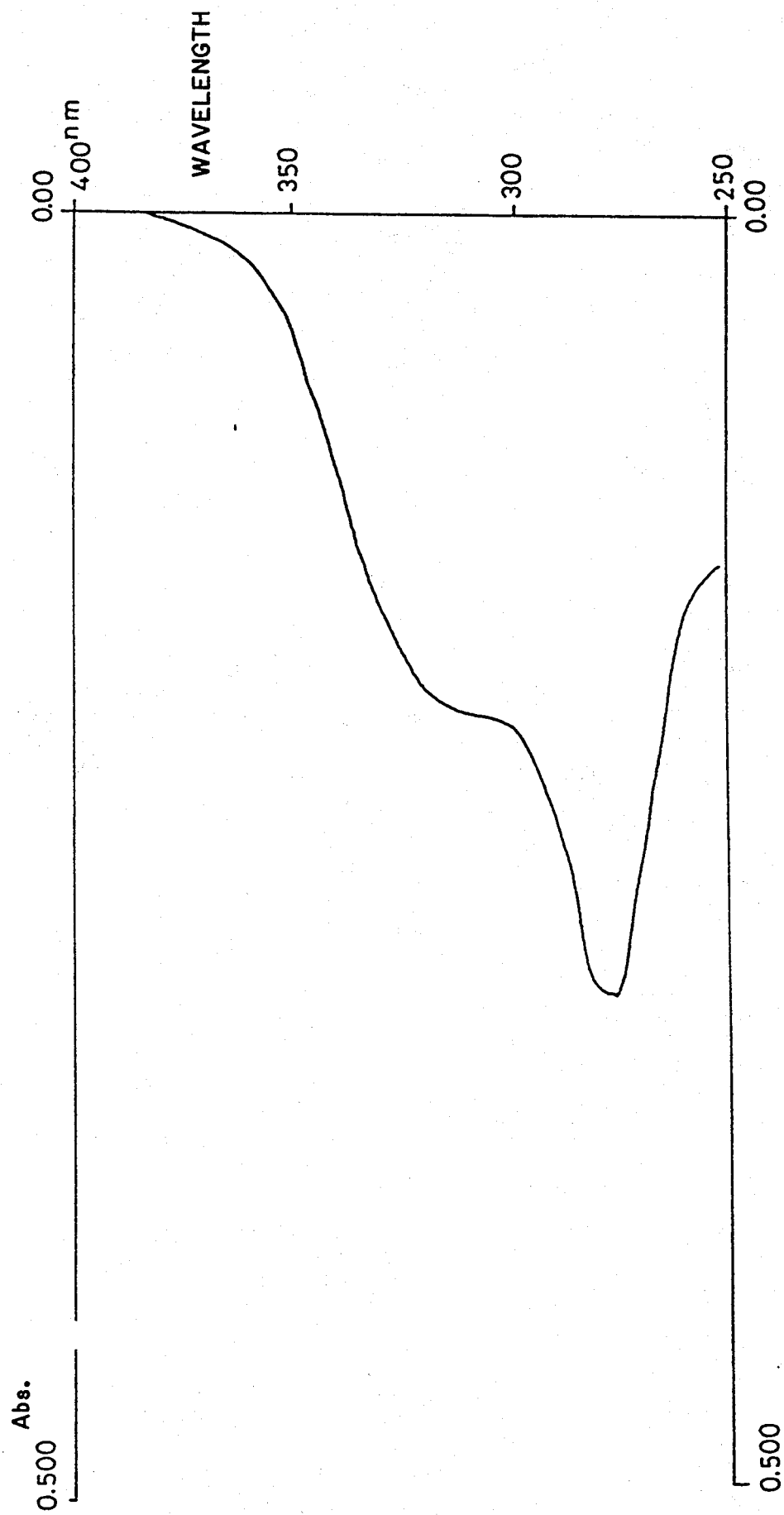
FIG. 8 is a chart of ultraviolet absorption spectrum of 1-(4-benzoyl-3-hydroxy-phenyl) glycerol maltitolether according to an embodiment of the present invention.

The results was shown in FIG. 8.

(5) Phenol indication

The product was spotted on TCL, phenol indicator was sprayed with a sprayer on it. 10% sodium carbonate solution was sprayed over it, and a color indicating presence of phenol was observed.

Embodiment 3 4,4'-maltitoiloxyglyceroxy-2,2'hydroxy benzophenone 3.0 g of 2,2',4,4'-tetrahydroxy benzophenone and 31.1 g (0.075 mol) of epichlorohydrin were dissolved, and 2240.0 mg of sodium hydroxide was added to it. The reaction system was heated to 100° C. and then cooled to 95° C., and 1.34 g of the sodium hydroxide was added. Additional heating and agitation were continued for 3 hours. Then the system was cooled to the room temperature, and salt was removed by filtering. The obtained filtrate was condensed under reduced pressure condition and purified according to the silica gel chromatography. 3.21 g of 4,4'-diglycidyloxy-2,2'-hydroxy benzophenone in solid state was obtained.

Then, 1.550 g of maltitol and 84.2 mg of potassium hydroxide were dissolved in 10 ml of dimethylsulfoxide, and heating and agitation were carried out for 30 minutes. A solution obtained by dissolved 606.0 mg of 4,4'-diglycidyloxy-2,2'-hydroxy benzophenone in 7 ml of dimethylsulfoxide was dripped. Furthermore, heating and agitation were continued for 1 hour under flow of nitrogen. The reaction system was cooled to the room temperature, and neutralized by chloric acid. The reaction system was fractionated according to the column chromatography using the hyperporous polymer (Hiporous resin supplied from Mitsubishi Kasei Kogyo Kabushiki Kaisha) with at first purified water as a developed solvent and then ethyl alcohol and purified water in which the mixing ratio of ethyl alcohol and purified water was 1:1. The effluent section in which the mixing ratio of ethyl alcohol and purified water was 1:1 was condensed, and 780 mg of 4,4'-maltitoiloxyglyceroxy-2,2'-hydroxybenzophenone was obtained.

Experiment 1 Production of Skin Lotion

According to the formulation as shown in table 1, a skin lotion in which the benzophenone derivative was mixed, and a skin lotion in which 2-hydroxy-4-methoxy-5-sulfoxisonium benzophenone as a control were produced.

TABLE 1

| COMPONENT | EXAMPLE 1 | CONTROL 1 |
|---|---|---|
| A. (ALCOHOL PHASE) | | |
| Ethanol | 5.0 | 5.0 |
| POE oleil alcohol ether | 2.0 | 2.0 |
| Perfume | q.s. | q.s. |
| B. (AQUEOUS PHASE) | | |
| 1,3-butylene glycerol | 5.0 | 5.0 |
| Benzophenone derivative (Embodiment 1) | 8.0 | — |
| 2-hydroxy-4-methoxy-sulfoxonium benzophenone | — | 8.0 |
| Triethanol amine | 0.1 | 0.1 |
| Carboxy vinyl polymer | 0.15 | 0.15 |
| Purified water | Residual | Residual |

Alcohol phase A was added to aqueous phase B, and a perfume was made water soluble to obtain a skin lotion.

In example 1, a skin lotion which has not color and is transparent with viscosity was obtained, while in control 1 a lotion which was yellow color and has no viscosity was obtained.

Experiment 2 Test for Anti-suntan Material

Field test were carried out in a sea beach using 2 types of skin lotion produced in Experiment 1. In the experiment, the sample were applied to right and left halves of each member of a group consisting of 20 men and 20 women. A degree of sun burning degree was determined. The criteria for the determination was as follows.

| Criteria for evaluation of sun-burning degree | |
|---|---|
| Remarkable erythema recognized | × |
| Slight erythema recognized | Δ |
| Erythema not recognized | ○ |

The results are shown in Table 2.

TABLE 2

| | APPLIED SECTION IN EXAMPLE 1 | APPLIED SECTION IN CONTROL 1 |
|---|---|---|
| ○ | 37 | 6 |
| Δ | 3 | 12 |
| × | 0 | 22 |
| NUMBER OF SKIN TROUBLE CASES | NONE | ITCH 10 CASES ERUPTION 2 CASES |

From the results as described above, the external preparation for skin in which the benzophenone derivative is mixed is more effective for protection from ultraviolet rays than that in which the prior types of water soluble ultraviolet absorbent are mixed, and has higher safety without causing any skin trouble.

Experiment 3 Capability to Preserved Humidity

Change of skin conductance in a group consisting of 15 men and 15 women were measured under the environmental condition of the room temperature of 25° C. and the relative humidity of 50%. The skin lotion produced in Experiment 1 was applied to an arm of each member of the group, and the skin conductance of the arm skin was measured in 24 hours after the treatment. The capability to preserve humidity was determined according to the increase ratio. Result of the determination were as follows.

$$\text{Increase rate of conductance} = \frac{\text{Increase ratio of conductance value}}{\text{Conductance value before treatment}}$$

Criteria for the capablility to preserve humidity

Increase ratio of conductance: less than 15%  ○
Increase ratio of conductance: 15% to 30%  Δ
Increase ratio of conductance: 30% or more  ○

The results are shown in Table 3. 1

TABLE 3

| | APPLIED SECTION IN EXAMPLE 1 | APPLIED SECTION IN CONTROL 1 |
|---|---|---|
| ○ | 21 | 6 |

TABLE 3-continued

| | APPLIED SECTION IN EXAMPLE 1 | APPLIED SECTION IN CONTROL 1 |
|---|---|---|
| Δ | 9 | 8 |
| × | 0 | 16 |

From the results as described above, it was turned out that the external preparation for skin with the benzophenone derivative according to the present invention mixed therein is more excellent in its capability to preserve humidity than the external preparation with the prior types of water soluble ultraviolet absorbent.

Embodiment 4 2-Hydroxy 4-(2-maltoxyethoxy) benzophenone 1 g of 2,4-dihydroxy benzophenone was added to and dissolved in 7 g of ethylbromohydrin, 37 mg of sodium hydroxide and 0.25 g of purified water. The solution was heated to 100° C. and stirred and then cooled to 90° C. Furthermore, 224 mg of sodium hydroxide was added to the mixture. The mixture was heated and stirred for 2 hours, and then cooled. The resultant was extracted with chloroform, washed with water, and condensed by removing the water. The product was purified using the silica gel chromatography (Toluene: Methylethyl ketone), and 1.1 g of 2-hydroxy 4-(2-hydroxyethoxy) benzophenone was obtained.

Then, 100 mg of the product was dissolved in 1 ml of toluene, and 219 mg of acetylmaltose and 10 mg of molybdoric acid were added. The resultant product was heated and stirred for 30 minutes under the temperature of 100° C. Then the reaction system was cooled by air to the room temperature, extracted by toluene, and the extract was washed once with purified water and 4 times with saturated saline, and the organic layer was dried with sulfuric magnesium anhydride and condensed under reduced pressure condition. The residual materials are purified according to the silica gel chromatography (Hexan: Ethyl acetate), and 110 mg of acetylated compound of 2-hydroxy 4-(2-maltosiloxyethoxy) benzophenone was obtained. 100 mg of this acetylated 2-hydroxy 4-(2-maltosiloxy) benzophenone was dissolved in 3 ml of methanol, 0.3 ml of natorium methylate was added to the mixture. The resultant mixture was stirred for 30 minutes under the room temperature, neutralized by an ion-exchange resin (such as, for instance, Umberlite IR 120B supplied from Organo Kogyo or UBK 530 from Mitsubishi Kasei), and the resin was removed by filtering. The reactant liquid was condensed under reduced pressure condition, and 2-hydroxy 4-(2-maltosiloxyethoxy) benzophenone was obtained. The resultant 2-hydroxy 4-(2-maltosiloxyethoxy) benzophenone was analyzed according to the methods (1) to (6).

(1) Infrared absorption spectroscopy

Measurement was made by using the IRA-1 infrared absorption spectrometer supplied from Nihon Bunko Kabushiki Kaisha with the KBr disk method, and absorption due to stretching vibration of the hydroxyl group at 3400 cm$^{-1}$, stretching vibration of the 2-maltosiloxyethoxy group at 2920 cm$^{-1}$ and stretching vibration of the carbonyl group at 1630 cm$^{-1}$ were observed.

Figure 9:
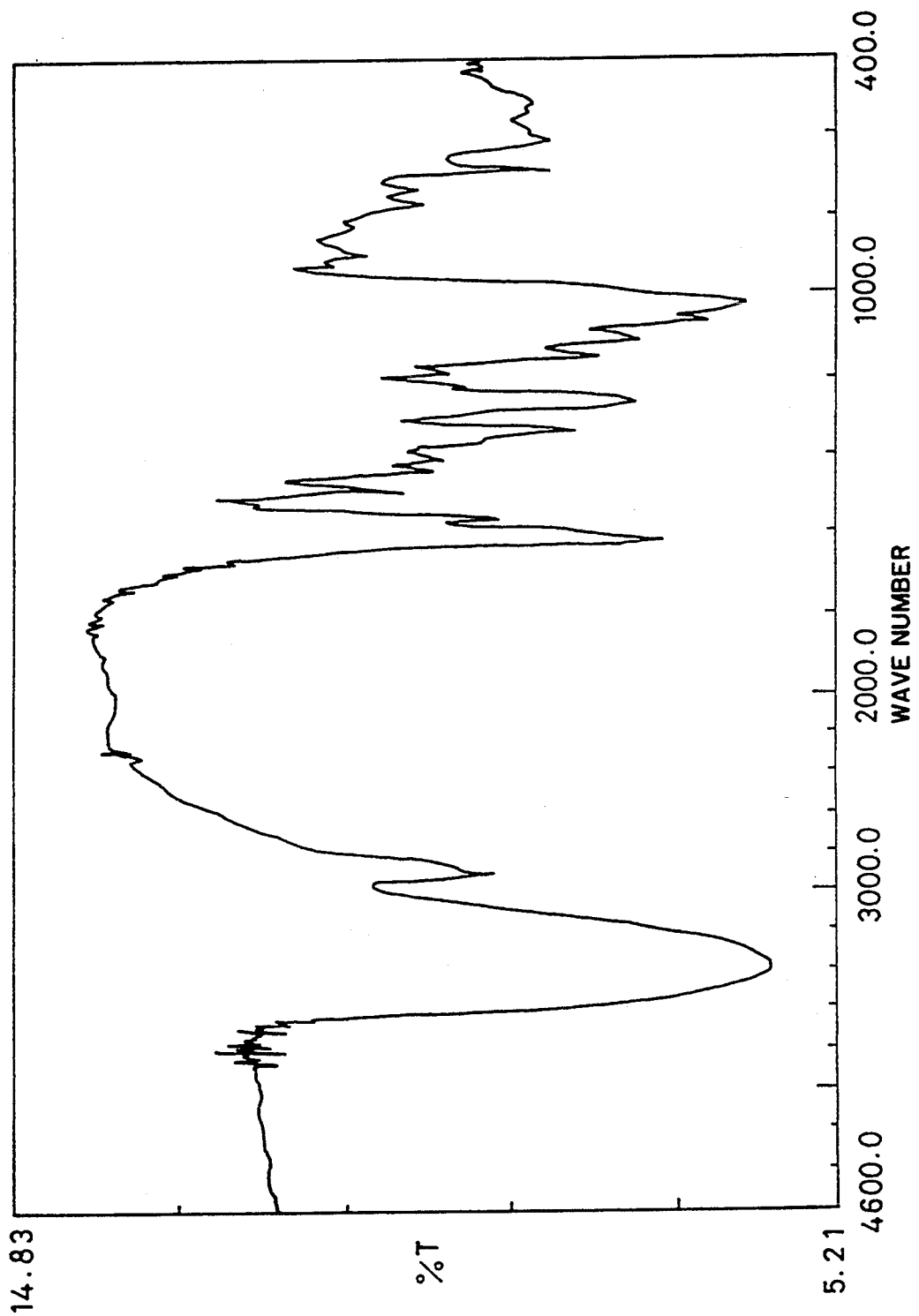
FIG. 9 is a chart of an infrared absorption spectrum of 2-hydroxy-4-(2-maltosiloxyethoxy) benzophenone according to an embodiment of the present invention.

The results are shown in FIG. 9.

(2) $^{13}$C-NMR spectroscopy

Measurement was made by using CD$_3$OD as a solvent with JOEL GX-400 from Nippon Denshi Kabushiki Kaisha at room temperature, and signal were observed at δ201 ppm, 167 ppm, 167 ppm, 140 ppm, 136 ppm, 133 ppm, 130 ppm, 129 ppm, 115 ppm, 108 ppm, 105 ppm, 103 ppm, 103 ppm, 81 ppm, 78 ppm, 77 ppm, 75 ppm, 75 ppm, 75 ppm, 74 ppm, 74 ppm, 72 ppm, 69 ppm, 69 ppm, 63 ppm, and 62 ppm.

Figure 10:
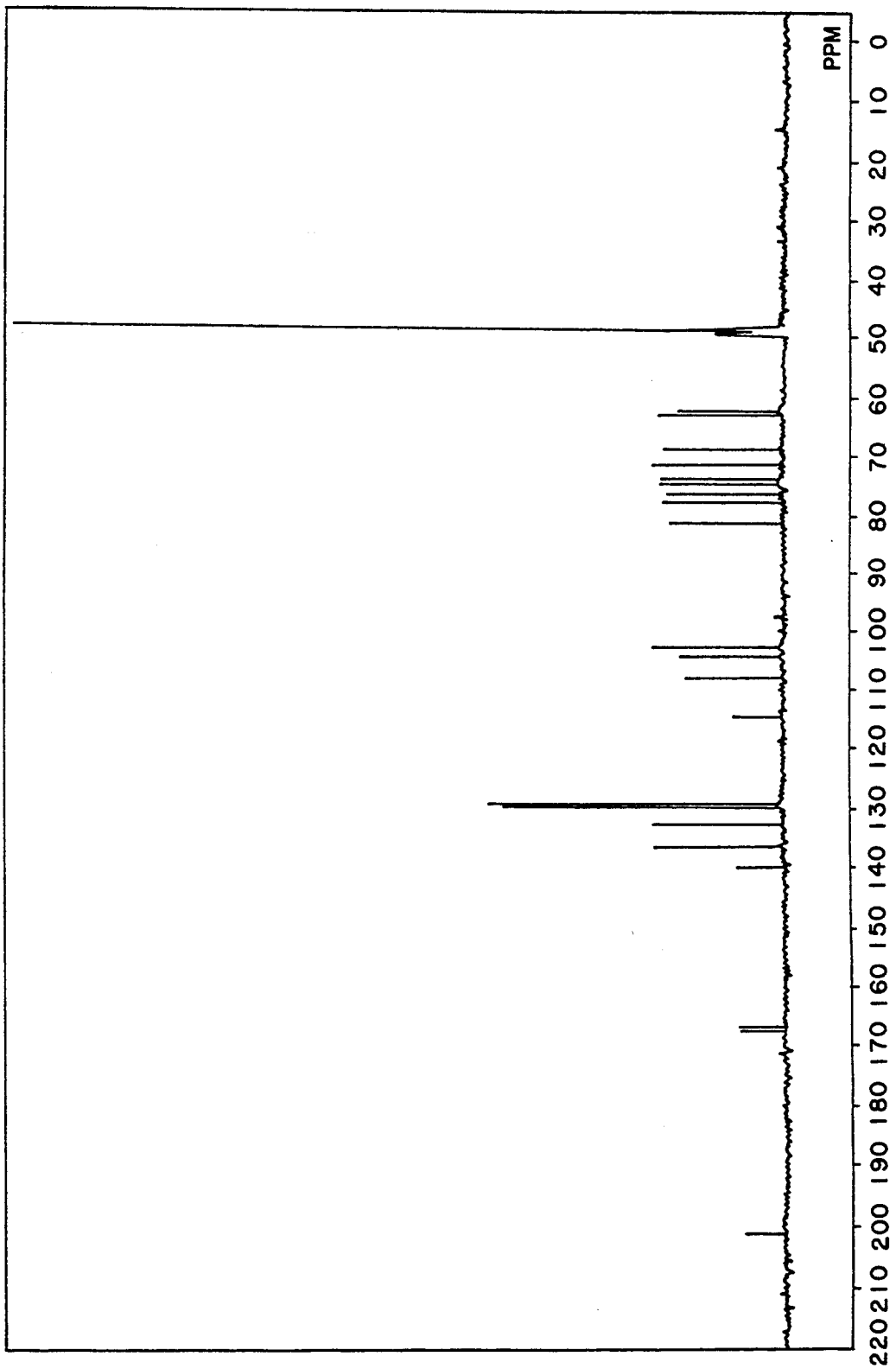
FIG. 10 is a chart of $^{13}$C-NMR spectrum of 2-hydroxy-4-(2-maltosiloxyethoxy) benzophenone according to an embodiment of the present invention.

The resultant are shown in FIG. 10.

(3) $^1$H-NMR spectroscopy

Measurement was made by using $CD_3OD$ as a solvent with JOEL GX-400 supplied from Nippon Denshi Kabushiki Kaisha under room temperature, and signals were observed at δ7.53-7.38 ppm, 6.46 to 6.39, and 4.72 to 3.11.

Figure 11:
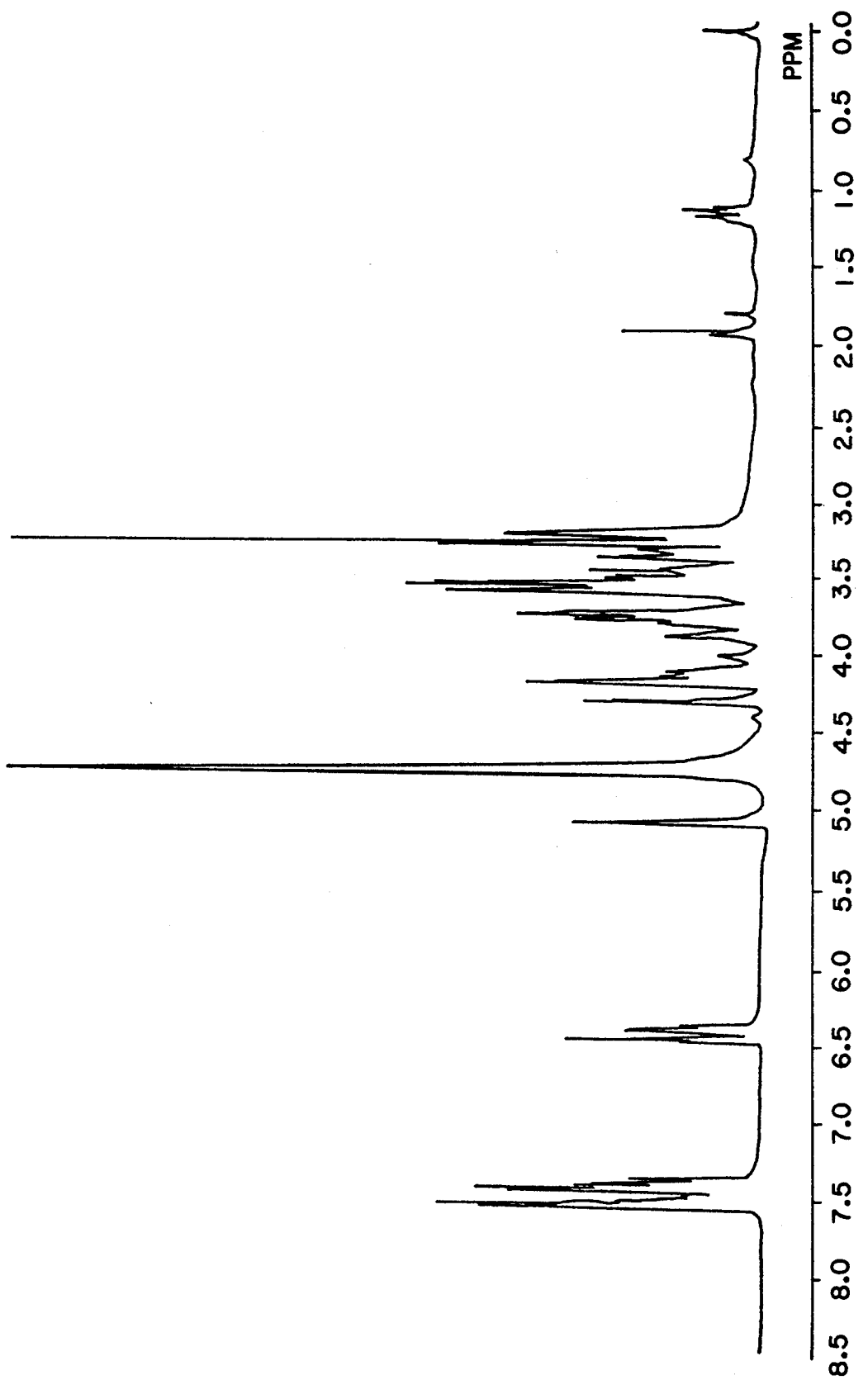
FIG. 11 is a chart of $^{1}$H-NMR spectrum of 2-hydroxy-4-(2-maltosiloxyethoxy) benzophenone according to an embodiment of the present invention.

The resultant are shown in FIG. 11.

(4) Ultraviolet ray absorption spectroscopy

Measurement was made by using the UVIDEC 610 C ultraviolet absorption spectrometer from Nihon Bunko Kabushiki Kaisha with methanol as a solvent, and the peak absorption was observed at 287.6 nm and 324.6 nm.

Figure 12:
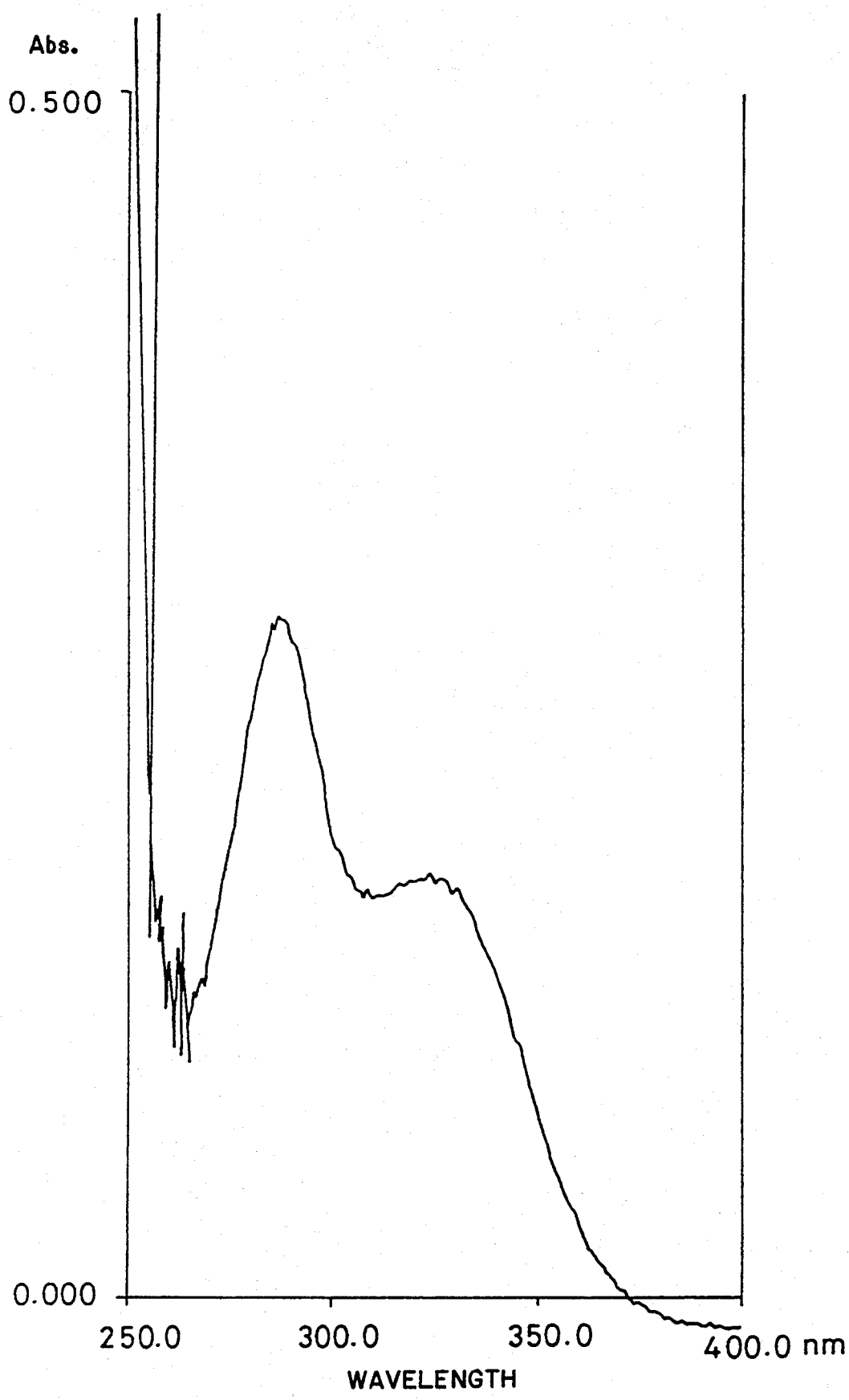
FIG. 12 is a chart of ultraviolet absorption spectrum of 2-hydroxy-4-(2-maltosiloxyethoxy) benzophenone according to an embodiment of the present invention.

The results was shown in FIG. 12.

(5) Melting point

Measuring was carried out by using the melting point measuring device based on a capillary system from Arthur H. Thoms Company, and the material was melted in the temperature range of 92° to 110° C., but a clear melting pint was not shown.

(6) Water solubility 20 weight % or more was dissolved in water.

Embodiment 5 2-hydroxy 4-(2-glucosiloxyethoxy) benzophenone 100 mg of the 2-hydroxy 4-(2-hydroxyethoxy) benzophenone synthesized in the Embodiment 4 was dissolved in 2 ml of toluene, 136 mg of acetylglucose was added to the mixture, and the resultant mixture was heated to 100° C., 50 mg of molybdoric acid was added to it, and the resultant mixture was heated and stirred for 30 minutes under the temperature of 100° C. The reaction system was air cooled to the room temperature, extracted by toluene, washed once with purified water and 4 times with saturated saline, and the organic layer was dried with sulfuric magnesium anhydride and was condensed under reduced pressure condition. The residual materials were purified according to the silica gel chromatography (Hexan: Ethylacetate), and 189 mg of acetylide of 2-hydroxy 4-(2-glycosiloxyethoxy) benzophenone was obtained.

189 mg of the acetylated 2-hydroxy 4-(2-maltosiloxyethoxy) benzophenone was dissolved in 6 ml of methanol, 0.6 ml of the sodium methylate was added to it, and the resultant mixture was stirred for 30 minutes under room temperature, neutralized by an ion-exchange resin (such as, for instance, Umbarlite IR120B from Organo Kogyo, or UBK 530 from Mitsubishi Kasei), the resin was removed by filtering, the reactant liquid was condensed under reduced pressure condition, and 2-hydroxy 4-(2-glucosiloxyethoxy) benzophenone was obtained. The obtained 2-hydroxy 4-(2-glucosiloxyethoxy) benzophenone was analyzed according to the method (1) to (6) described below.

(1) Infrared absorption spectroscopy

Measurement was made by using the IRA-1 infrared absorption spectrometer supplied from Nihon Bunko Kabushiki Kaisha with the KBr disk method, and absorption due to stretching vibration of the hydroxyl group at 3400 cm$^{-1}$, stretching vibration of the 2-glucosiloxyethoxy group at 2930 cm$^{-1}$, and stretching vibration of the carbonyl group at 1630 cm$^{-1}$ were observed.

Figure 13:
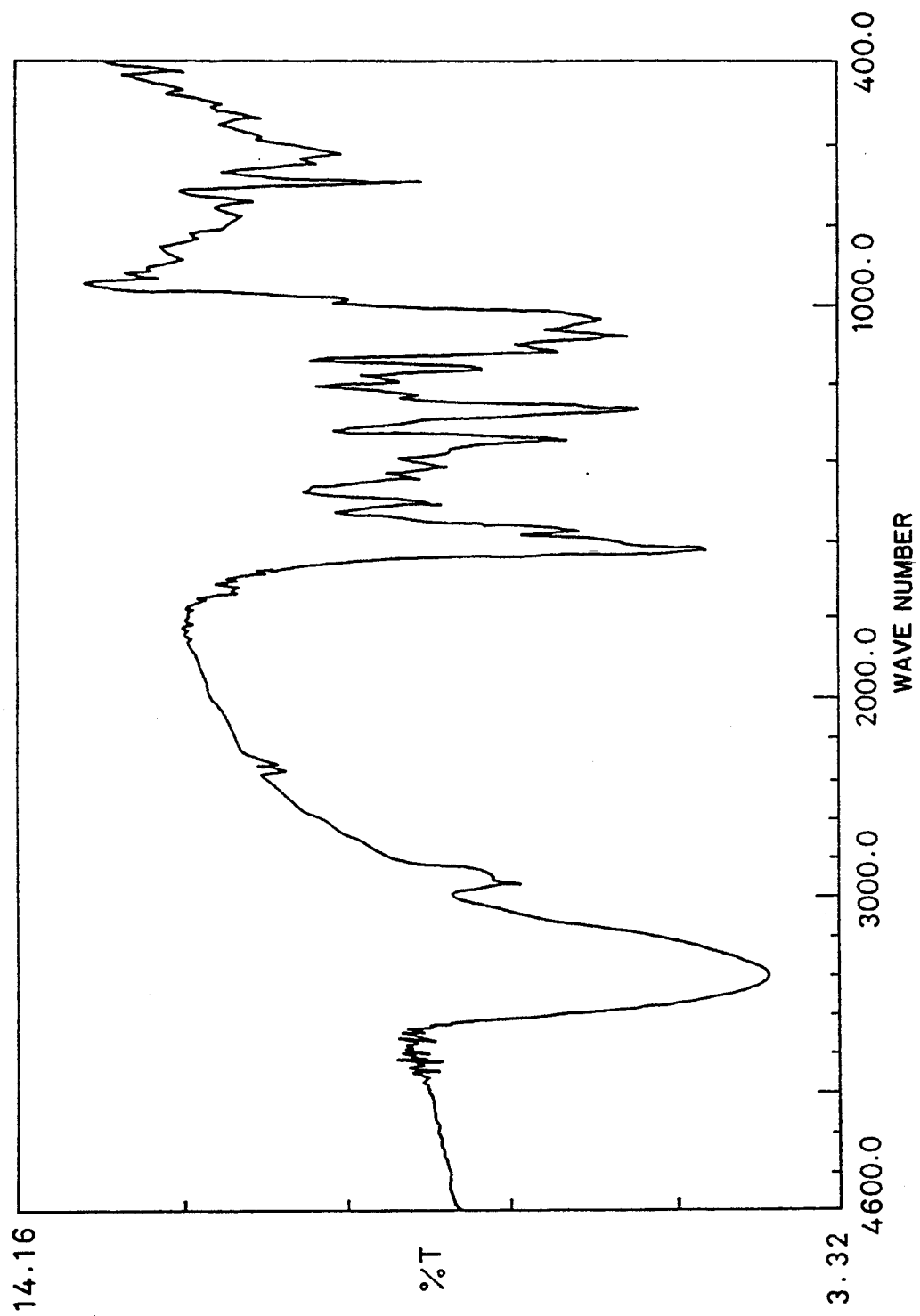
FIG. 13 is a chart of an infrared absorption spectrum of 2-hydroxy-4-(2-glucosiloxyethoxy) benzophenone according to an embodiment of the present invention.

The results are shown in FIG. 13.

(2) $^{13}$C-NMR spectroscopy

Measurement was made by using $CD_3OD$ as a solvent with JOEL GX-400 from Nippon Denshi Kabushiki Kaisha at room temperature, and signal were observed at δ201 ppm, 167 ppm, 167 ppm, 140 ppm, 136 ppm, 133 ppm, 130 ppm, 129 ppm, 114 ppm, 109 ppm, 108 ppm, 104 ppm, 103 ppm, 78 ppm, 75 ppm, 72 ppm, 69 ppm, 69 ppm, and 62 ppm.

Figure 14:
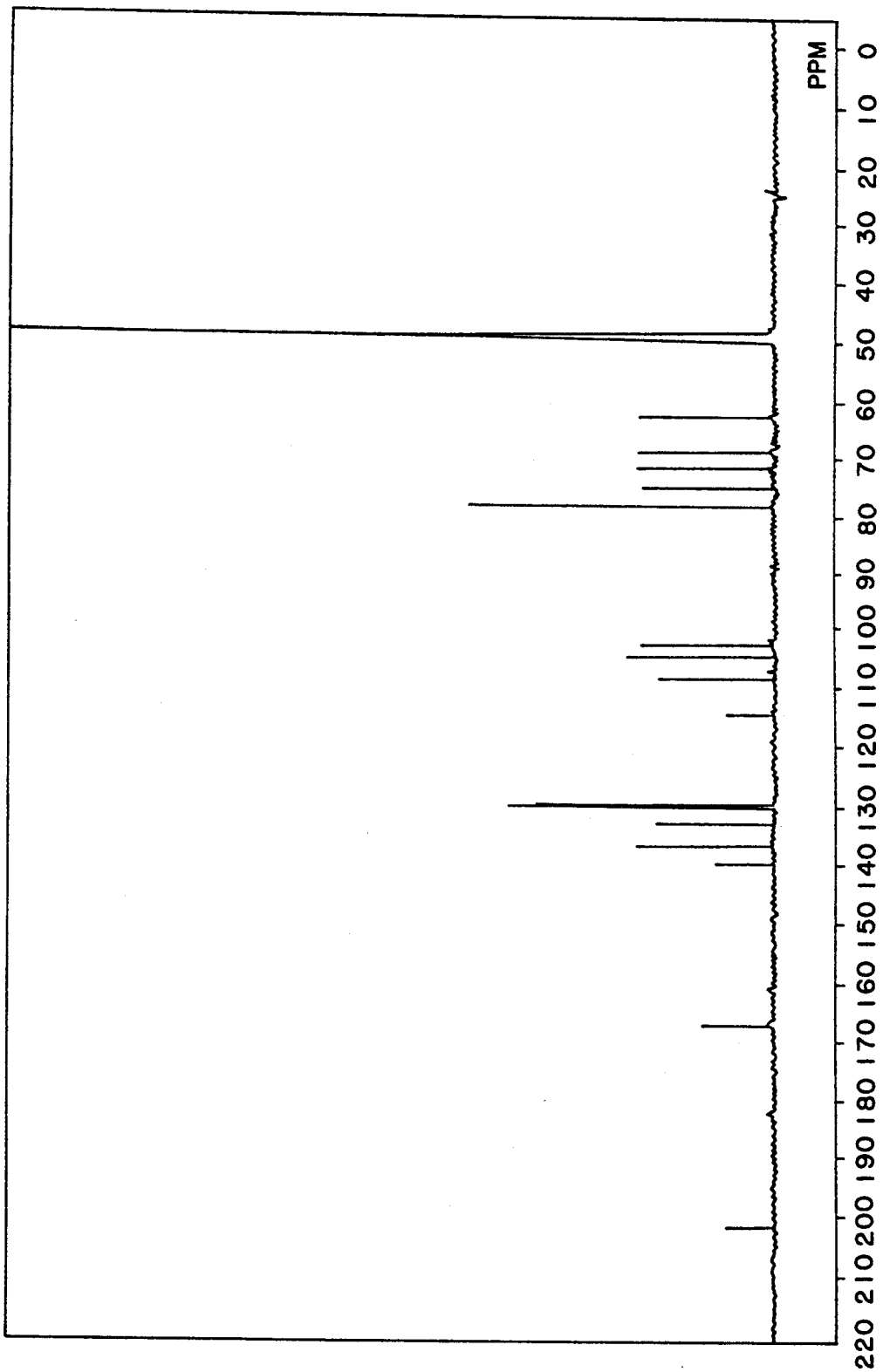
FIG. 14 is a chart of $^{13}$C-NMR spectrum of 2-hydroxy-4-(2-glucosiloxyethoxy) benzophenone according to an embodiment of the present invention.

The resultant are shown in FIG. 14.

(3) $^1$H-NMR spectroscopy

Measurement was made by using $CD_3OD$ as a solvent with JOEL GX-400 supplied from Nippon Denshi Kabushiki Kaisha, and signals were observed at δ7.52-7.38 ppm, 6.45 to 6.39, and 4.28 to 3.10.

Figure 15:
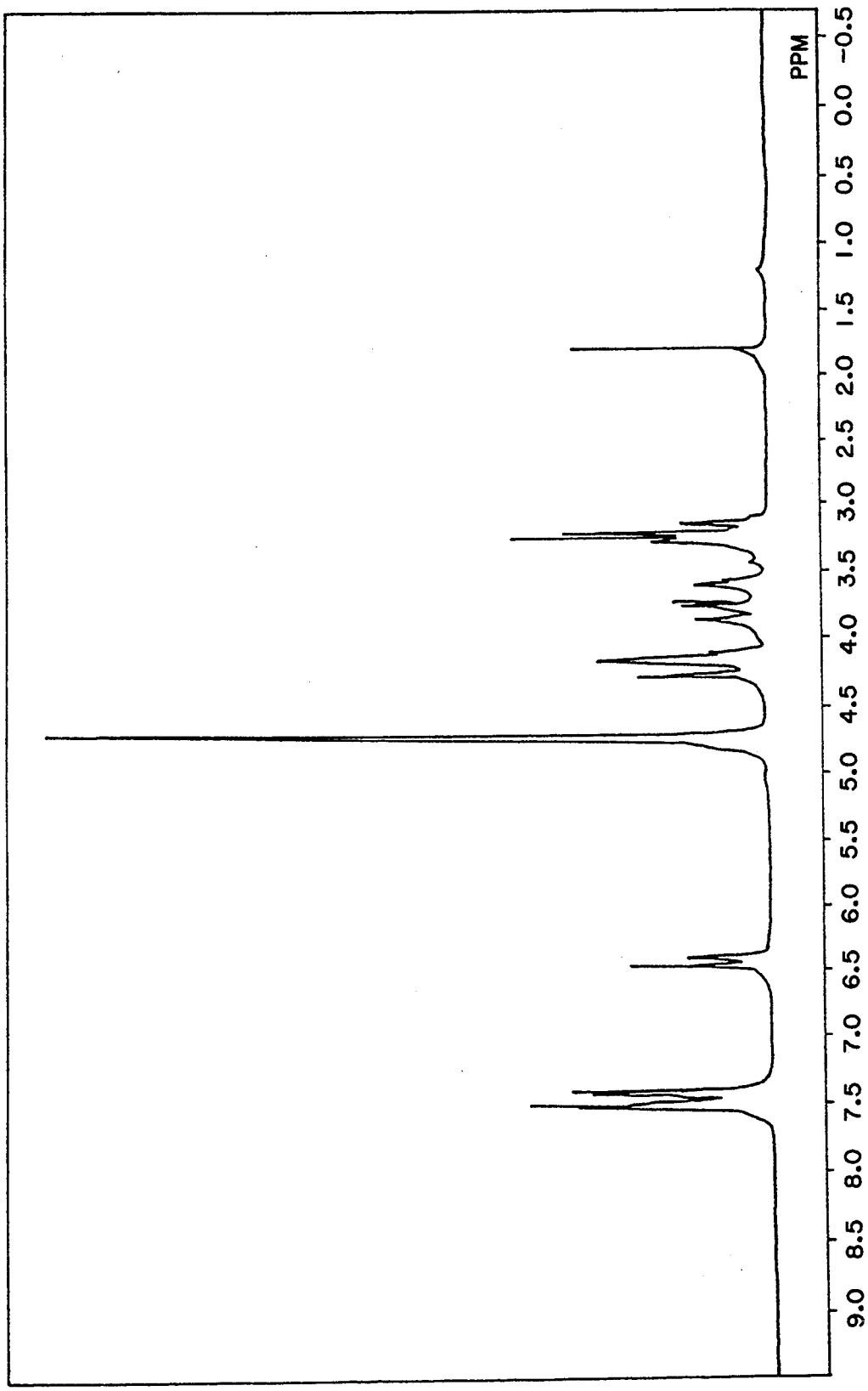
FIG. 15 is a chart of $^{1}$H-NMR spectrum of 2-hydroxy-4-(2-glucosiloxyethoxy) benzophenone according to an embodiment of the present invention.

The resultant are shown in FIG. 15.

(4) Ultraviolet ray absorption spectroscopy

Measurement was made by using the UVIDEC 610 C ultraviolet absorption spectrometer from Nihon Bunko Kabushiki Kaisha with methanol as a solvent, and the peak absorption was observed at 286.9 nm and 324.3 nm.

Figure 16:
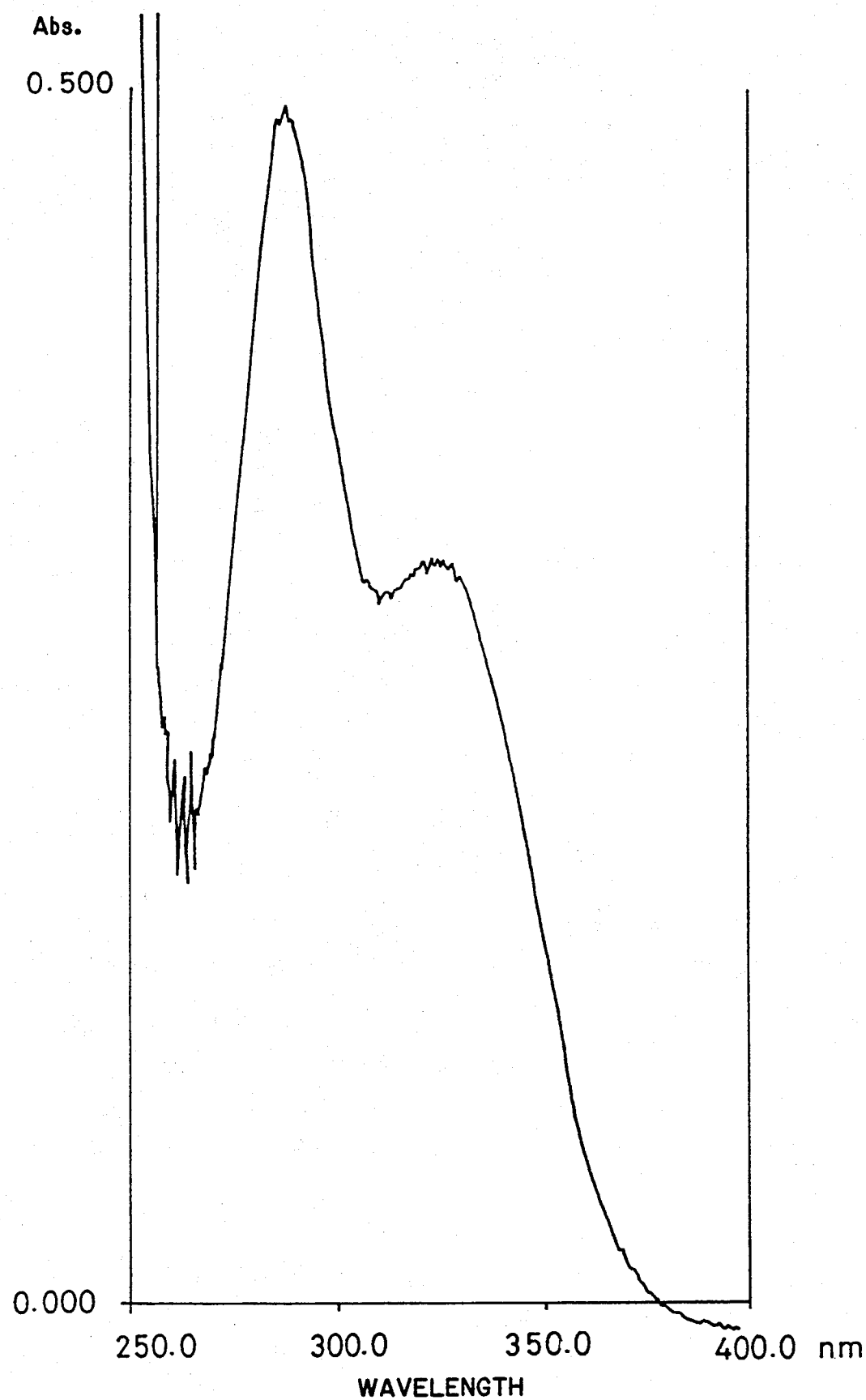
FIG. 16 is a chart of ultraviolet absorption spectrum of 2-hydroxy-4-(2-glucosiloxyethoxy) benzophenone according to an embodiment of the present invention.

The results was shown in FIG. 16.

(5) Melting point

The compound absorbs much humidity, and measurement could not be carried out.

(6) Water solubility

The compound was dissolved in water by around 10 weight %.

Embodiment 6 2-hydroxy 4-(3-maltosiloxypropyroxy) benzophenone 1 g of 2,4-dihydroxy benzophenone was dissolved with 7.78 g of 1-bromopropanol, 40 mg of sodium hydroxide, and 0.1 ml of purified water. The mixture was heated to 100° C. and stirred, and was cooled to 90° C. Furthermore 220 mg of sodium hydroxide was added. The mixture was heated and stirred for 4 hours, and then air cooled, extracted by chloroform, washed with water, and then dried and condensed. The product was purified by using the silica gel column chromatography (Toluene: Methylethyl ketone), and 1.01 g of 2-hydroxy 4-(3-hydroxypropyroxy) benzophenone was obtained (Yield: 80%).

1.14 g of octaacetyl maltose was added to 460 mg of 2-hydroxy 4-(3-hydroxypropyroxy) benzophenone, and the mixture was dissolved in 10 ml of toluene, and heated to 90° C., and then a catalystic level of molybdoric acid was added to it. The mixture was heated and stirred for 30 minutes and then air cooled, extracted with 100 ml of toluene, and washed with saturated sodium bicarbonate water. After dried and condensed, the product was purified by the silica gel chromatography (Toluene: Methylethyl ketone), and 880 mg of acetylide of 2-hydroxy 4-(3-maltosiloxypropyroxy) benzophenone was obtained (Yield: 60%).

880 mg of the acetylide of 2-hydroxy 4-(3-maltosiloxypropyroxy) benzophenone was dissolved in 20 ml of methanol, sodium methoxide was added. The mixture was stirred for 30 minutes and then neutralized by acidic resin, filtered and condensed and 565 mg of 2-hydroxy 4-(3-maltosiloxypropyroxy) benzophenone was obtained (Yield: 100%).

The 2-hydroxy 4-(3-maltosiloxypropyroxy) benzophenone was confirmed according to the methods (1) to (6) described below.

(1) Infrared absorption spectroscopy

Measurement was made by using the IRA-1 infrared absorption spectrometer supplied from Nihon Bunko Kabushiki Kaisha with the KBr disk method, and absorption due to stretching vibration of the hydroxyl group at 3400 cm$^{-1}$, stretching vibration of the 3-maltosiloxy group at 2930 cm$^{-1}$, and stretching vibration of the carbonyl group at 1626 cm$^{-1}$ were observed.

Figure 17:
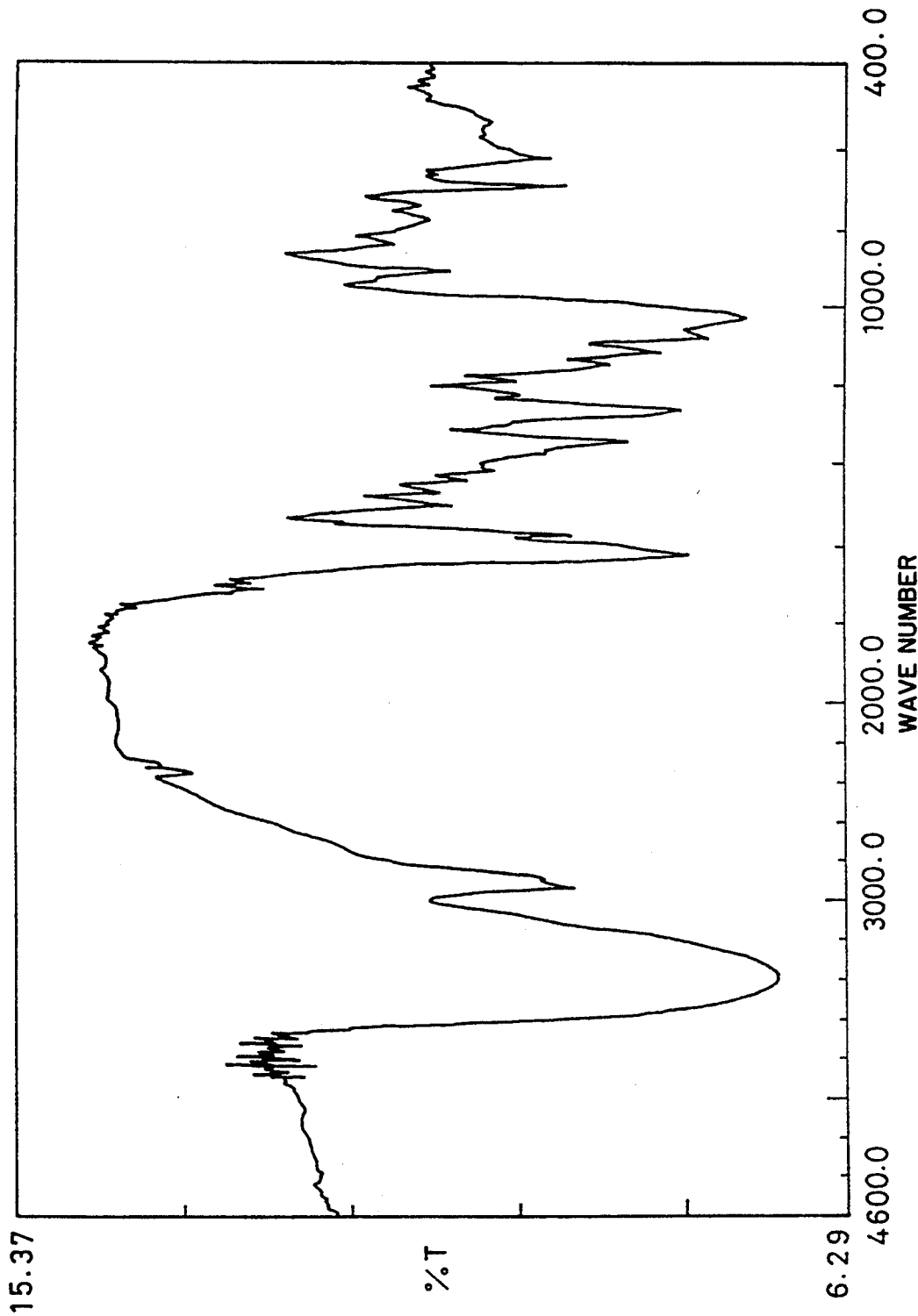
FIG. 17 is a chart of an infrared absorption spectrum of 2-hydroxy-(3-maltosiloxypropyloxy) benzophenone according to an embodiment of the present invention.

The results are shown in FIG. 17.

(2) $^{13}$C-NMR spectroscopy

Measurement was made by using CD$_3$OD as a solvent with JOEL GX-400 from Nippon Denshi Kabushiki Kaisha under room temperature, and signal were observed at δ201 ppm, 167 ppm, 167 ppm, 140 ppm, 136 ppm, 133 ppm, 130 ppm, 129 ppm, 114 ppm, 109 ppm, 104 ppm, 103 ppm, 81 ppm, 78 ppm, 76 ppm, 75 ppm, 75 ppm, 74 ppm, 71 ppm, 67 ppm, 67 ppm, 63 ppm, 62 ppm, and 30 ppm.

Figure 18:
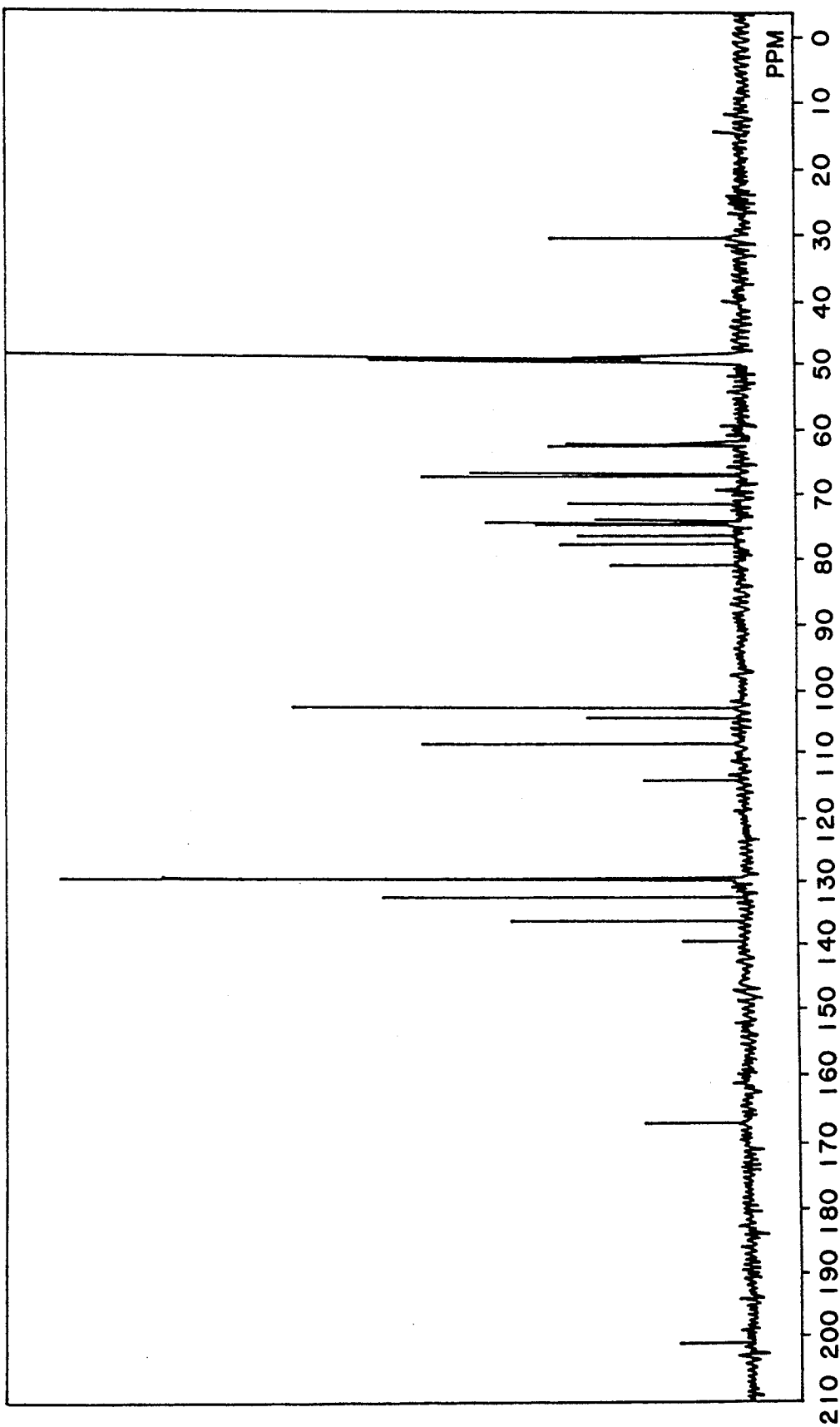
FIG. 18 is a chart of $^{13}$C-NMR spectrum of 2-hydroxy-(3-maltosiloxypropyloxy) benzophenone according to an embodiment of the present invention.

The resultant are shown in FIG. 18.

(3) $^1$H-NMR spectroscopy

Measurement was made by using CD$_3$OD as a solvent with JOEL GX-400 supplied from Nippon Denshi Kabushiki Kaisha under room temperature, and signals were observed at δ7.55 ppm, 7.50 ppm, 7.43 ppm, 6.56 ppm, 6.50 ppm, 6.44 ppm, and in a range from 5.22 ppm to 1.9 ppm.

Figure 19:
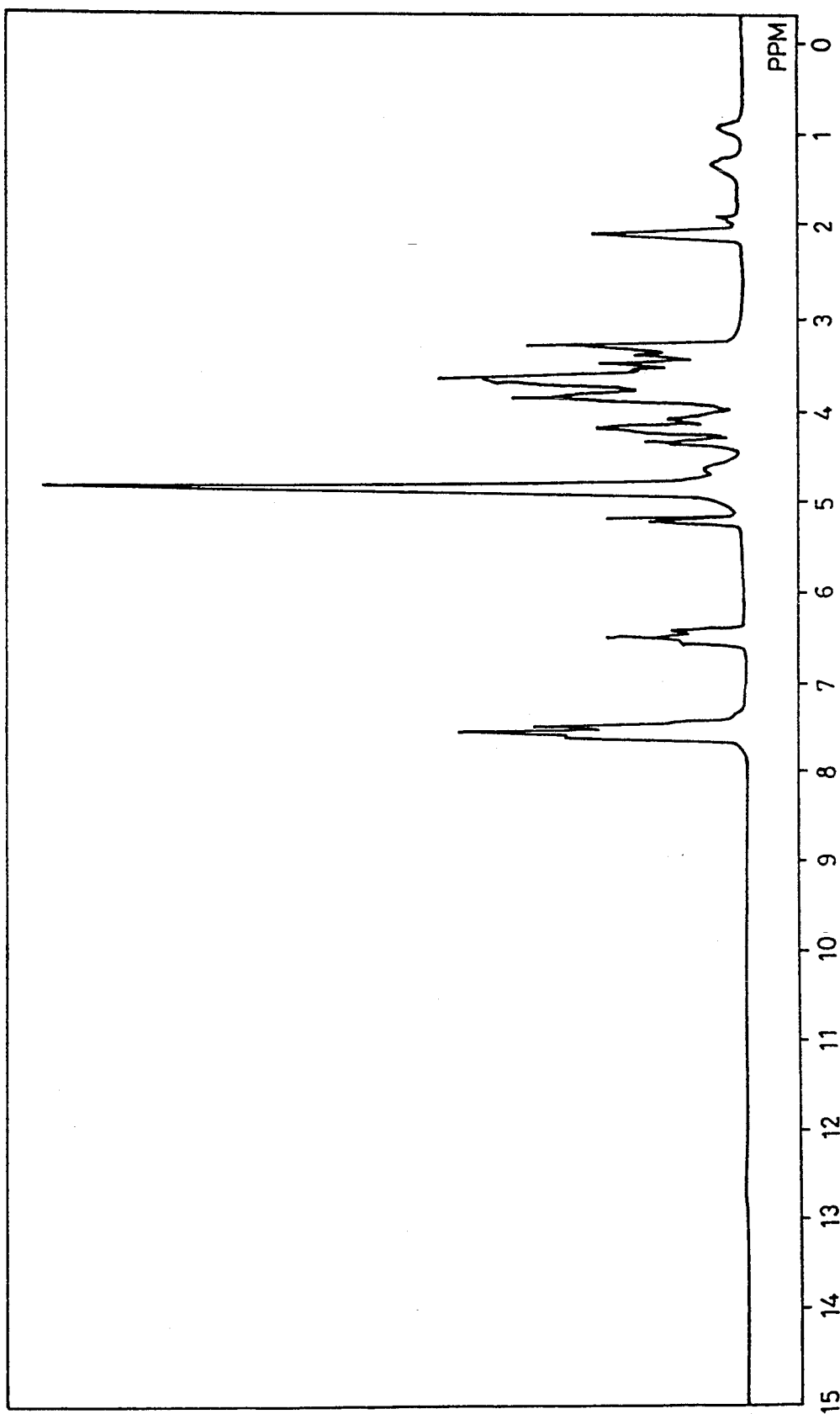
FIG. 19 is a chart of $^{1}$H-NMR spectrum of 2-hydroxy-(3-maltosiloxypropyloxy) benzophenone according to an embodiment of the present invention.

The resultant are shown in FIG. 19.

(4) Ultraviolet ray absorption spectroscopy

Measurement was made by using the UVIDEC 610 C ultraviolet ray absorption spectrometer from Nihon Bunko Kabushiki Kaisha with methanol as a solvent, and the peak absorption was observed at 289.4 nm and 324.1 nm.

Figure 20:
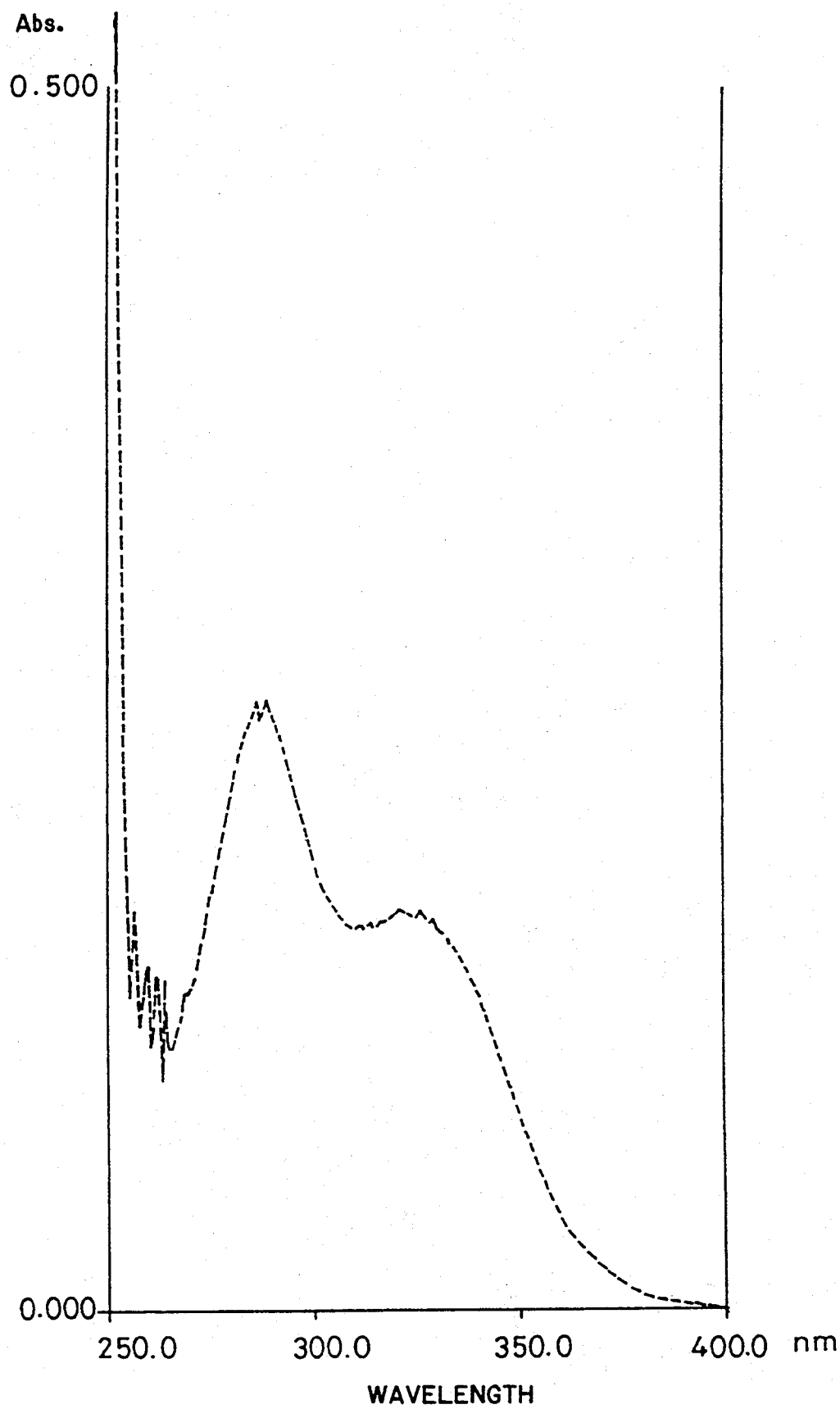
FIG. 20 is a chart of ultraviolet absorption spectrum of 2-hydroxy-(3-maltosiloxypropyloxy) benzophenone according to an embodiment of the present invention.

The results was shown in FIG. 20.

(5) Melting point

Measurement was made by using the melting point measuring device based on a capillary system developed by Arthur H. Thomas Company, and the product was melted in temperature range from 77° to 87° C., but a clear melting point was not shown.

(6) Water solubility

The compound was dissolved in water by around 20 weight % or more.

Experiment 4 Production of Skin Lotion

According to the formulation as shown in table 4, a skin lotion in which the benzophenone derivative was mixed, and a skin lotion in which 2-hydroxy-4-methoxy-5-sulfoxisonium benzophenone as a control ware produced.

TABLE 4

| COMPONENT | EXAMPLE 2 | CONTROL 1 |
|---|---|---|
| A (ALCOHOL PHASE) | | |
| Ethanol | 5.0 | 5.0 |
| POE oleil alcohol ether | 2.0 | 2.0 |
| Perfume | q.s. | q.s. |
| B (AQUEOUS PHASE) | | |
| 1,3-butylene glycerol | 5.0 | 5.0 |
| Benzophenone derivative (Embodiment 4) | 8.0 | — |
| 2-hydroxy-4-methoxy-sulfoxonium benzophenone | — | 8.0 |
| Triethanol amine | 0.1 | 0.1 |
| Carboxy vinyl polymer | 0.15 | 0.15 |
| Purified water | Residual | Residual |

Alcohol phase A was added to aqueous phase B, and a perfume was made water soluble to obtain a skin lotion.

In example 2, an excellent skin lotion which is transparent and viscosity without any specific color, while in control 2 a lotion which was yellow color and has no viscosity was obtained.

Experiment 5 Test for Anti-suntan Material

Field test were carried out in a sea beach using 2 types of skin lotion produced in Experiment 4. In the experiment, the sample were applied to right and left halves of each member of a group consisting of 20 men and 20 women. A degree of sun burning was determined. The criteria for the determination of a degree of burning by sunlight and other condition are the same as those in Experiment 2 above.

The results are shown in Table 5.

TABLE 5

| | APPLIED SECTION IN EXAMPLE 2 | APPLIED SECTION IN CONTROL 2 |
|---|---|---|
| ○ | 39 | 6 |
| Δ | 1 | 15 |
| × | 0 | 19 |
| NUMBER OF SKIN TROUBLE CASES | NONE | ITCH 8 CASES ERUPTION 2 CASES |

From the results as described above, the external preparation for skin in which the benzophenone derivative is mixed is more effective for protection from ultraviolet rays than that in which the prior types of water soluble ultraviolet absorbent are mixed, and has higher safety without causing any skin trouble.

Experiment 6 Capability to Preserved Humidity

The capability of the product to preserve humidity was tested according to the same procedure as that in experiment 3 above.

The results are as shown in Table 6.

TABLE 6

| | APPLIED SECTION IN EXAMPLE 2 | APPLIED SECTION IN CONTROL 2 |
|---|---|---|
| ○ | 26 | 6 |
| Δ | 4 | 8 |
| × | 0 | 16 |

From the results as described above, it was turned out that the external preparation for skin with the benzophenone derivative according to the present invention mixed therein is more excellent in its capability to preserve humidity than the external preparation with the prior types of water soluble ultraviolet absorbent.

Description is made for examples of mixing in the external preparation for skin according to the present invention. It should be noted that each external preparations showed an excellent effect for preventing ultraviolet rays.

| Embodiment 7 Cream | |
|---|---|
| A. Oily phase | |
| Stearic acid | 10.0 |
| Stearyl alcohol | 4.0 |
| Stearic acid monoglycerin | 8.0 |
| Vitamin E acetate | 0.5 |
| Perfume | 0.4 |

-continued

| Embodiment 7 Cream | |
|---|---|
| Ethyl paraben | 0.1 |
| Butyl paraben | 0.1 |
| Propyl paraben | 0.1 |
| B. Aqueous phase | |
| Propylene glycol | 8.0 |
| Glycerin | 2.0 |
| 1-(4-benzoyl-3-hydroxy phenyl) glycerol maltitolether | 6.0 |
| Potassium hydroxide | 0.4 |
| Trisodium edetate | 0.05 |
| Purified water | Residual |

Production method

The oily fraction A and the aqueous fraction B are heated to 70° C. and completely dissolved. Then phase A is added to phase B, and the mixture is emulsified by a emulsifier. Then the emulsion is cooled by a heat exchanger and the cream is obtained.

| Embodiment 8 Cream | |
|---|---|
| A. Oily phase | |
| Cetanol | 4.0 |
| Vaseline | 7.0 |
| Isopropyl milistate | 8.0 |
| Squalane | 12.0 |
| Dimethyl polysiloxane | 3.0 |
| Stearic acid monoglycerin ester | 2.2 |
| POE(20) solbitane monostearate | 0.5 |
| Glycyrrhyzin acid stearate | 0.1 |
| BHT | 0.02 |
| Ethylparaben | 0.1 |
| Butylparaben | 0.1 |
| Propylparaben | 0.1 |
| B. Aqueous phase | |
| 1,3 butylene glycol | 7.0 |
| Disodium edetate | 0.07 |
| Phenoxyethanol | 0.2 |
| L-ascorbic acid phosphoric acid ester magnesium salt | 3.0 |
| Polyacrylic acid alkyl ester | 1.0 |
| 1-(4-benzoylphenyl) glycerol maltitolether | 8.0 |
| Purified water | Residual |

Production method

The cream was obtained according to the procedure as in the Embodiment 7.

| Embodiment 9 Milky Lotion | |
|---|---|
| A. Oily phase | |
| Oleylorate | 3.0 |
| Vaseline | 7.0 |
| Squalane | 5.0 |
| Sorbitane-sesqui-oleic acid ester | 0.8 |
| Polyoxyethylene oleil ether (20 E.O.) | 1.2 |
| 1-(4-benzoyl-3-hydroxy phenyl) glycerol solbitol ether | 3.0 |
| Methylparaben | 0.1 |
| Perfume | 0.12 |
| B. Aqueous phase | |
| Dipropylenglycol | 5.0 |
| Ethanol | 3.0 |
| Carboxy vinyl polymer | 0.17 |
| Sodium hyrluronate | 0.01 |
| Polyacrylic alkyl ester | 1.0 |
| 1-(4-benzoyl-3-hydroxy phenyl) glycerol sugar ether | 4.0 |
| Potassium hydroxide | 0.08 |
| Hexametalic acid sodium | 0.05 |
| Purified water | Residual |

Production method

The milky lotion was obtained according to the same procedure as in the Embodiment 7.

| Embodiment 10 Cream | |
|---|---|
| A. Oily phase | |
| Behenyl alcohol | 0.5 |
| 12-hydroxy stearic acid cholestanol ester | 2.0 |
| Squalane | 7.0 |
| Jojoba oil | 5.0 |
| Self-emulsifying type monostearic acid glycerin | 2.5 |
| Polyoxyethylene sorbithane monestearic acid ester(2OEO) | 1.5 |
| 2-hydroxy-4-methoxy benzophenone | 3.0 |
| Ethylparaben | 0.2 |
| Butylparaben | 0.1 |
| Propylparaben | 0.1 |
| B. Aqueous phase | |
| Propylene glycol | 5.0 |
| Sodium edetate | 0.08 |
| Glycerin | 5.0 |
| Beegum (Montmorillonite) | 3.0 |
| Potassium hydroxide | 3.3 |
| 1-(4-benzoyl-3-hydroxyphenyl) glycerol maltotriol ether | 8.0 |
| Purified water | Residual |

Production method

The cream was obtained according to the same procedure as in the Embodiment 7.

| Embodiment 11 Skin Lotion with powder | |
|---|---|
| A. Oily phase | |
| Ethanol | 8.0 |
| POE(60) glyceril monoisostearate | 2.0 |
| L-menthol | 0.1 |
| Campher | 0.1 |
| Methylparaben | 0.2 |
| Perfume | q.s. |
| B. Aqueous phase | |
| Glycerin | 3.5 |
| 1-(4-benzoyl phenyl) glycerol maltotriolether | 4.0 |
| Zinc | 1.5 |
| Kaolin | 0.5 |
| 12-hydroxy stearic acid cholestanol ester | 2.0 |
| Squalane | 7.0 |
| Jojoba oil | 5.0 |
| Self-emulsifying type monostearic acid glycerin | 2.5 |
| Polyoxyethylene sorbithane monestearic acid ester(2OEO) | 1.5 |
| 2-hydroxy-4-methoxy benzophenone | 3.0 |
| Ethylparaben | 0.2 |
| Butylparaben | 0.1 |
| Propylparaben | 0.1 |
| B. Aqueous phase | |
| Propylene glycol | 5.0 |
| Sodium edetate | 0.08 |
| Glycerin | 5.0 |
| Beegum (Montmorillonite) | 3.0 |
| Potassium hydroxide | 3.3 |
| 2,2',4'-trihydroxy-4(2-maltosiloxyethoxy) benzophenone | 8.0 |
| Purified water | Residual |

Production method

The cream was obtained according to the same procedure as in the Embodiment 7.

| Embodiment 16 Skin Lotion with powder | |
|---|---|
| A. Oily phase | |
| Ethanol | 8.0 |
| POE(60) glyceril monoisostearate | 2.0 |
| L-menthol | 0.1 |
| Campher | 0.1 |
| Bentonite | 0.3 |
| Sodium hexamethalate | 0.03 |

| Embodiment 16 Skin Lotion with powder | |
|---|---|
| Purified water | Residual |

Production method
The skin lotion was obtained according to the same procedure as that in Embodiment 7.

| Embodiment 12 Cream | |
|---|---|
| A. Oily phase | |
| Stearic acid | 10.0 |
| Stearyl alcohol | 4.0 |
| Stearic acid monoglycerin | 8.0 |
| Vitamin E acetate | 0.5 |
| Perfume | 0.4 |
| Ethyl paraben | 0.1 |
| Butyl paraben | 0.1 |
| Propyl paraben | 0.1 |
| B. Aqueous phase | |
| Propylene glycol | 8.0 |
| Glycerin | 2.0 |
| 2-hydroxy 4-(2-maltosiloxyethoxy) Benzophenone | 8.0 |
| Potassium hydroxide | 0.4 |
| Trisodium edetate | 0.05 |
| Purified water | Residual |

Production method
The cream was obtained according to the same procedure as in the Embodiment 7.

| Embodiment 13 Cream | |
|---|---|
| A. Oily phase | |
| Cetanol | 4.0 |
| Vaseline | 7.0 |
| Isopropyl milistate | 8.0 |
| Squalane | 12.0 |
| Dimethyl polysiloxane | 3.0 |
| Stearic acid monoglycerin ester | 2.2 |
| POE(20) solbitane monostearate | 0.5 |
| Glycyrrhyzin acid stearate | 0.1 |
| BHT | 0.02 |
| Ethylparaben | 0.1 |
| Butylparaben | 0.1 |
| Propylparaben | 0.1 |
| B. Aqueous phase | |
| 1,3 butylene glycol | 7.0 |
| Disodium edetate | 0.07 |
| Phenoxyethanol | 0.2 |
| L-ascorbic acid phosphoric acid ester magnesium salt | 3.0 |
| Polyacrylic acid alkyl ester | 1.0 |
| 2-hydroxy-4-(2-glyceroilethoxy) benzophenone | 8.0 |
| Purified water | Residual |

Production method
The cream was obtained according to the procedure as in the Embodiment 7.

| Embodiment 14 Milky Lotion | |
|---|---|
| A. Oily phase | |
| Oleylorate | 3.0 |
| Vaseline | 7.0 |
| Squalane | 5.0 |
| Sorbitane-sesqui-oleic acid ester | 0.8 |
| Polyoxyethylene oleyl ether (20 E.O.) | 1.2 |
| Di-p-methoxy cinnamic acid glycerol | 3.0 |
| Methylparaben | 0.1 |
| Perfume | 0.12 |
| B. Aqueous phase | |
| Dipropylenglycol | 5.0 |
| Ethanol | 3.0 |
| Carboxy vinyl polymer | 0.17 |

| Embodiment 14 Milky Lotion | |
|---|---|
| Sodium hyrluronate | 0.01 |
| Polyacrylic alkyl ester | 1.0 |
| 2,2'-dihydroxy 4-(2-maltosiloxyethoxy) benzophenone | 4.0 |
| Potassium hydroxide | 0.08 |
| Hexametalic acid sodium | 0.05 |
| Purified water | Residual |

Production method
The milky lotion was obtained according to the same procedure as in the Embodiment 7.

| Embodiment 15 Cream | |
|---|---|
| A. Oily phase | |
| Behenyl alcohol | 0.5 |
| Methylparaben | 0.2 |
| Perfume | q.s. |
| B. Aqueous phase | |
| Glycerin | 3.5 |
| 2-hydroxy-4(3-maltosiloxybuthoxy) benzophenone | 4.0 |
| Zinc | 1.5 |
| Kaolin | 0.5 |
| Bentonite | 0.3 |
| Sodium hexamethalate | 0.03 |
| Purified water | Residual |

Production method
The skin lotion was obtained according to the same procedure as that in Embodiment 7.

As described above, the benzophenone derivatives according to the present invention have excellent capability to absorb ultraviolet rays as well as high compatibility with polar solvent.

Also, the external preparation for skin in which the materials are mixed can be mixed in a polar base, which insures wide availability for industrial purpose.

What is claimed is:

1. Benzophenone derivative expressed by the following general expression (1):

wherein A in the above general expression (1) is a residual group having 4 or more carbon atoms obtained by removing one hydroxyl group from sugar or sugar alcohol, n is 1 to 3, and B is a benzophenone group shown by the following general expression (2)

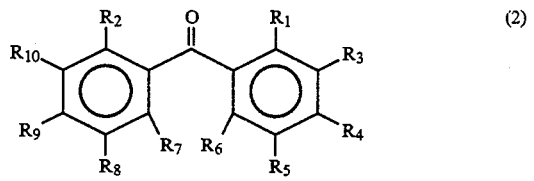

wherein $R_1$ through $R_{10}$ each is expressed by hydrogen, hydroxyl group, an alkoxy group having 1 to 4 carbon atoms, or the aforesaid binder $\underline{C}$, and at least one of them is the binder $\underline{C}$, and $\underline{C}$ is —O—R, O is oxygen, R is 1 to 4 carbon atoms, or 1 mole of glycerin with one hydroxyl group herein bound to A and another hydroxyl group to B.

2. Ultraviolet absorbent contains one or more of the benzophenone derivatives according to claim 1.

3. External preparation for skin contains one or more of benzophenone derivatives according to claim 1.

4. Benzophenone derivatives expressed by the following general expression (3):

 (3)

wherein A in the above general expression (3) is a residual group having 4 or more carbon atoms obtained by removing one hydroxyl group from sugar or sugar alcohol, and B is a benzophenone group shown by the following general expression (4);

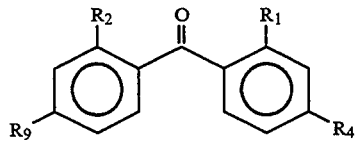 (4)

wherein at one of $R_1$ through $R_9$ in the general expression (4) is a group bound C, and the others are hydrogen, an alkyl group, or an alkoxy group;

C is equivalent to 1 mole or glycerin with one hydroxyl group therein bound to A and another hydroxyl group to B; and n is 1 to 3.

5. Ultraviolet absorbent contains one or more of the benzophenone derivatives according to claim 4.

6. External preparation for skin contains one or more of benzophenone derivatives according to claim 4.

7. Benzophenone derivatives expressed by the following general expression (7):

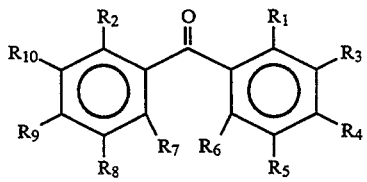 (7)

wherein $R_1$ and $R_2$ each is hydrogen or hydroxyl group, and at least one of them is expressed by a hydroxyl group;

$R_3$ to $R_{10}$ each is hydrogen, a hydroxyl group, or —O—R—A and at least one of them is expressed by the —O—R—A, in case of an alkoxy group, the number of carbon atoms is 1 to 4, A is a residual group obtained by removing one hydroxyl group from sugar, and R is 1 to 4 carbon atoms.

8. Ultraviolet absorbent contains one or more of the benzophenone derivatives according to claim 7.

9. External preparation for skin contains one or more of benzophenone derivatives according to claim 7.

* * * * *